(12) United States Patent
Libove et al.

(10) Patent No.: US 11,089,964 B1
(45) Date of Patent: Aug. 17, 2021

(54) METHOD AND APPARATUS FOR NON-INVASIVE REAL-TIME BIOMEDICAL IMAGING OF NEURAL AND VASCULAR ACTIVITY

(71) Applicant: Furaxa, Inc., Berkeley, CA (US)

(72) Inventors: Joel Libove, Orinda, CA (US); Mike Ingle, Albany, CA (US); David Schriebman, Berkeley, CA (US)

(73) Assignee: Furaxa, Inc., Berkeley, CA (US)

( * ) Notice: Subject to any disclaimer, the term of this patent is extended or adjusted under 35 U.S.C. 154(b) by 0 days.

(21) Appl. No.: 16/863,728

(22) Filed: Apr. 30, 2020

Related U.S. Application Data

(62) Division of application No. 14/885,236, filed on Oct. 16, 2015, now Pat. No. 10,660,531.

(51) Int. Cl.
  *A61B 5/021* (2006.01)
  *A61B 5/352* (2021.01)
  *A61B 5/369* (2021.01)

(52) U.S. Cl.
  CPC .............. *A61B 5/021* (2013.01); *A61B 5/352* (2021.01); *A61B 5/369* (2021.01)

(58) Field of Classification Search
  CPC ................................. A61B 5/021; A61B 5/369
  See application file for complete search history.

(56) References Cited

U.S. PATENT DOCUMENTS

| | | | |
|---|---|---|---|
| 2014/0171811 A1* | 6/2014 | Lin ....................... | A61B 5/7278 600/485 |
| 2014/0276031 A1* | 9/2014 | Lomnitz ............... | A61B 5/4312 600/430 |
| 2016/0007862 A1* | 1/2016 | Ku ....................... | A61B 5/0402 600/301 |

* cited by examiner

*Primary Examiner* — Jason M Ip
(74) *Attorney, Agent, or Firm* — Rimon Law, P.C.

(57) ABSTRACT

Biomedical images of both anatomical structure and real-time changes in neuronal, metabolic, positional, and vascular function in humans and animals is described. Ultra-wideband (UWB) pulse or square wave generators and electrical samplers, implemented using integrated circuits are used to make arrays of miniaturized microwave modules that are placed around the portion of interest in the body or head, allowing images to be made through either time-domain transmission of these pulsed waves through the body, or time domain reflectivity of the waves from internal structures, or their combination. Signal processing separate and extract the time-varying functional information from the static structural image data. The time-varying functional information from certain brain regions can be interpreted in order to control prosthetics, Brain-Machine-Interfaces and the like.

4 Claims, 18 Drawing Sheets

FIG. 5 ──────── Increasing tissue depth ──────▶

Coaxial RF Probe Array for Small Animal Functional Neuroimaging

METHOD AND APPARATUS FOR NON-INVASIVE REAL-TIME BIOMEDICAL IMAGING OF NEURAL AND VASCULAR ACTIVITY

CROSS-REFERENCE TO RELATED APPLICATIONS

This application is a divisional application of U.S. patent application Ser. No. 14/885,236 filed on Oct. 16, 2015 and also entitled "Method and Apparatus for Non-Invasive Real-Time Biomedical Imaging of Neural and Vascular Activity," the disclosure of which is incorporated herein by reference.

BACKGROUND

Field of the Invention

The present invention is in the field of medical imaging and more particularly is directed to functional and structural medical imaging based on the transmission and reflection of short radio-frequency pulses, especially as applied to the brain, and applications thereof to medical testing as well as to user interfaces based on imaged brain activity.

Related Art

It is known that the diverse dielectric properties of biological tissues can be used to produce structural images of biological systems, such as the human body. It is also known that changes in dielectric properties of brain tissues may be measured continuously, and are indicative of changing concentrations of chemical substances, such as glucose, oxyhemoglobin and deoxyhemoglobin in various tissue regions. Additionally, it is known that when a neuron is excited it briefly expands, as do associated glial cells, such as astrocytes. When large groups of neurons in a region concurrently expand, this is manifest as a change in both the dielectric permittivity ($E_r$) and conductivity, and these changes respectively alter the electromagnetic propagation velocity and path attenuation of an electromagnetic wave traversing the region. For example, X. P. Li et al at National University of Singapore have transmitted microwave energy through the head of a rat, and observed changes in transmission that are hypothesized to be the result of changes in average dielectric constant $E_r$ in response to changes in overall neural activity in the rat's brain.

Low resolution images of changing concentrations of hemoglobin and other substances have been made using Near Infrared Radiation (NIR), and some fast shallow neural activity has been observed using Event Related Optical Spectroscopy (EROS). Microwave imaging, however, prior to the present invention has failed to provide real-time spatial measurements of functional operation in the brain.

It is known that pulse-based or square wave edge-based microwave imaging may be done using either time domain reflectivity (TDR) techniques or using time domain transmission (TDT) techniques. In the TDR technique, signals from a transmit antenna are launched either through air or through a coupling compound such as water, towards one surface of the body where they subsequently penetrate the body and then reflect off of various internal tissue boundaries that constitute an interface between different dielectric permittivities, and back to the same antenna or nearby antennae. In the TDT technique, a transmitter and antenna launch pulses into one side of the volume of interest, while a group of antennae and receivers elsewhere on the surface detect the signals that have traversed the body.

While, in the case of TDT, most of the RF energy traversing the body tissues will be lost or reflected, some will emanate from a distant surface, where it can be detected by an array of receiving antennae whose signals are captured using samplers that are actuated concurrently, causing them to take simultaneous, and periodically repeating, electrical snapshots of the received signal. It is also known that a transmitter and receiving sampler may be connected to a shared antenna, and each such subsystem can thus be used for TDR, TDT or a combination of both. The broad spatial radiation pattern of most microwave antennae causes the transmitted wavefront to be radiated, spreading outwards in a somewhat cone shaped path, through the body.

Prior art microwave medical imaging systems have generally been based on Vector Network Analyzers (VNAs) or other instruments which produce swept sine waves that are transmitted via broadband antennae into the body, and which concurrently record the resulting returned signals, via reflection or transmission, from the subject body region. To date, none has produced sharp images of deep structures within the human head or body. Also, these instruments are not sufficiently sensitive and do not have adequate signal collection efficiency to reliably detect, in real time, reflectivity or transmissivity changes in tissues that are due to functional changes due to neuronal, metabolic, or vascular changes, such as what would be measured by MEG, fMRI, fNIR, SPECT or PET.

These limitations of swept frequency microwave imaging systems are in part due to insufficient signal to noise ratio (SNR), due to the prohibitive expense of using a sufficiently large number of concurrently active TDR or Vector Network Analyzer channels and the sheer size of the large bundles of thick microwave cabling that would be required to operate concurrently to achieve acceptable signal collection efficiency. Additionally the SNR of VNAs is insufficient to achieve acceptable signal collection efficiency in the time frame required to accurately detect real-time neurally-modulated dielectric and mechanical changes in brain tissue. Dielectric changes include changes in permittivity and in conductivity, which depend on the frequency of the electromagnetic field traversing the tissue. Mechanical changes can include strain expansion and contraction of neuronal tissue as well as changes in the amplitude of the pulsations of their associated vascular structures. Prior art microwave imaging system using VNAs lack the sensitivity needed to detect these tiny changes, and hence, functional brain measurements using microwaves have not been usable for temporal studies of brain function nor for thought identification or control of prosthetic devices.

While prior art microwave imaging systems that use electrical pulses and sample apertures instead of swept sine waves produce potentially better images, to date these images have only been made for shallow structures in the body, such as for detecting breast tumors. To image deeper and detect the faint changes that occur in responses to neuronal activity requires still higher SNR. MRI, including fMRI, while enabling high resolution functional and structural images of the brain, and able to show functional and vascular activity, is non-portable and expensive. Additionally, the 1.5 to 4 second response time that is characteristic of fMRI is too slow to display millisecond-scale real-time neural activity. Also, MRI requires the patient to be exposed to several kilowatts of RF power, of which several watts of average power are absorbed by the head. While such absorbed energy has not been shown to be harmful, long term safety also has not been proven, and it would be desirable to have no more than milliwatts of RF power transmitted into the body. Finally, fMRI requires the subject to be confined within a large MRI machine, and remain still, and therefore cannot be used to study neural or vascular function in many operational environments, such as when performing physical tasks or job functions.

PET and SPECT both require expensive, non-portable scanners, and injection of radioactive tracers into the body. Both methods are also very slow, and therefore unusable for real-time studies of brain activity. fNIR and EROS imagers are semi-portable, and capable of near-real-time assessment of metabolic activity in the brain, but suffer from low resolution and a poor penetration depth of approximately 1 cm. EEG is capable of showing the summation of the real-time neural activity in a given region of the brain, but suffers from the inability to localize the source of said activity, particularly when concerning deep structures within the brain, and therefore is not considered a true imaging modality.

MEG is capable of real-time localization of neural activity in the brain, but requires a large expensive machine using superconducting detectors, and therefore is not usable in operational environments. ECoG involves the invasive placement of electrodes directly on the surface of the brain. In addition to the attendant patient risk due to the required surgeries, the electrodes eventually become non-functional, and ECoG only provides good source localization for regions near the electrode locations.

SUMMARY OF THE INVENTION

The invention relates generally to medical imaging systems and brain-computer-interfaces (BCIs) based on the use of short electrical pulses and microwave electrical sampling technology. The invention further relates to functional and structural medical imaging, based on the transmission and reflection of radio-frequency waves. It also relates to non-invasive real-time detection and imaging of activity in the brain for the control of external apparatus, including, for example, motor and speech prostheses.

The present invention overcomes the limitations of prior art microwave imaging systems by sending rapid sequences of custom-shaped microwave pulses into the body and detecting the resulting reflected and/or transmitted microwave energy in response to the pulses. The present invention consists of a configuration of interconnected small and low cost assemblies that each can provide microwave pulses, through either an antenna or radio-frequency (RF) probe, and have an antenna or RF probe and an electrical sampler to receive microwave energy. Various embodiments consist of a light-weight array of such assemblies where one or a few assemblies can be selected to produce a pulse and all or most assemblies receive the response. The present invention further consists of algorithms for combining the signal outputs from the samplers contained in one or more of said assemblies in order to directly measure neural, mechanical and vascular activity.

The microwave pulse trains from these assemblies, termed "pulser-antenna-sampler" (PAS) assemblies herein, provide orders of magnitude more efficient signal collection efficiency and resulting enhanced signal to noise ratios by concentrating both the transmitted and received energy into a broadband comb of very narrow frequency bands, and eliminating the susceptibility to noise at all other frequencies between these narrow comb teeth. A high pulse rate enables fewer comb teeth, each spaced further apart and each containing a higher energy density.

A heterodyning (down-converting) method generates, at the output of each sampler, a waveform that repeats at the difference frequency between the pulse rate and the sampling rate. Concurrently, this difference frequency is directly measured through the use of a simple, conventional, D-Flip-Flop, whose clock input is fed from a copy of the sampler clock, and whose D (data) input is fed from the pulser clock. The output from this flip-flop is a similarly heterodyned waveform, but in the form of a square wave having a frequency that is the difference frequency between the sampler and pulser clocks, and each rising edge of this square wave can be used to initiate (trigger) the capture of one heterodyned (downconverted) sampler output waveform, which can be performed by a conventional data acquisition system. By then repeatedly adding up a succession of these acquired sampler output waveforms, the data acquisition system can accumulate an average of many waveforms. If a number N of waveforms is thus averaged, the signal-to-noise ratio (SNR) of this combined waveform is improved, versus an individually captured waveform, typically by a factor of the square root of N, thereby improving the sensitivity of the imager.

It should be noted that although heterodyning is frequently described herein as being achieved by using pulser and sampler clocks running at offset frequencies, in other embodiments both clocks run at the same frequency but the sampler clock adds an incrementally increasing time offset after each transition, for instance generated by a conventional time Vernier (phase shifter), during the duration of the acquisition of the sampled waveform. The variable time offset added after each successive transition creates a delay between successive transitions that incrementally increases after each transition.

The microwave pulse trains from these PAS assemblies reflect off of structural boundaries in tissue, and travel at different rates of speed and with different degrees of signal attenuation in different types of tissues, and therefore the system respectively measures differences in both the timing and amplitude of the received microwave energy, and uses this information to map structural features of the brain. Some embodiments of the present invention include hundreds to thousands of such PAS assemblies, that when provided around a person's head, provide non-invasive whole brain scanning in a fraction of a second. On top of structural brain imaging, which can serve as a baseline, very short duration images can be compared against the baseline to reveal quickly evolving changes in the brain tissue due to metabolic, functional changes. Such changes in the motor cortex and in in speech regions, for example, can be detected and mapped in real time to functions such as muscle control and word creation. Such changes in other areas of the brain can be similarly monitored and utilized.

Functional brain imaging permits the use of brain activity to control external apparatus, and as such, the present invention provides a brain computer interface (BCI) that is far more capable than conventional units that use EEG and ECoG technology. In this way the invention can enable non-invasive and real-time external control of limbs, and the generation of speech in people with aphasia due to damage between the speech centers and vocal tract, for instance. Additionally, the present invention could form the basis of a general purpose mental user interface (MUI), capable of the detection and identification of thoughts and other mental activity.

Finally, the present invention has been demonstrated to be capable of measuring and displaying in real time, vascular and tissue motion due to arterial pulsation. Such changes in pulsation can be the result of changes in blood flow due to changing functional requirements of brain tissue. Additionally, changes in pulsatility measured at two diverse arterial locations may be used to infer arterial blood pressure. Further, if an abnormally high amplitude of pulsation is measured at a point along a vascular structure, this may indicate the possible presence of an abnormality such as an aneurism or arteriovenous (AV) malformation.

DETAILED DESCRIPTION OF THE INVENTION

Figure 1:
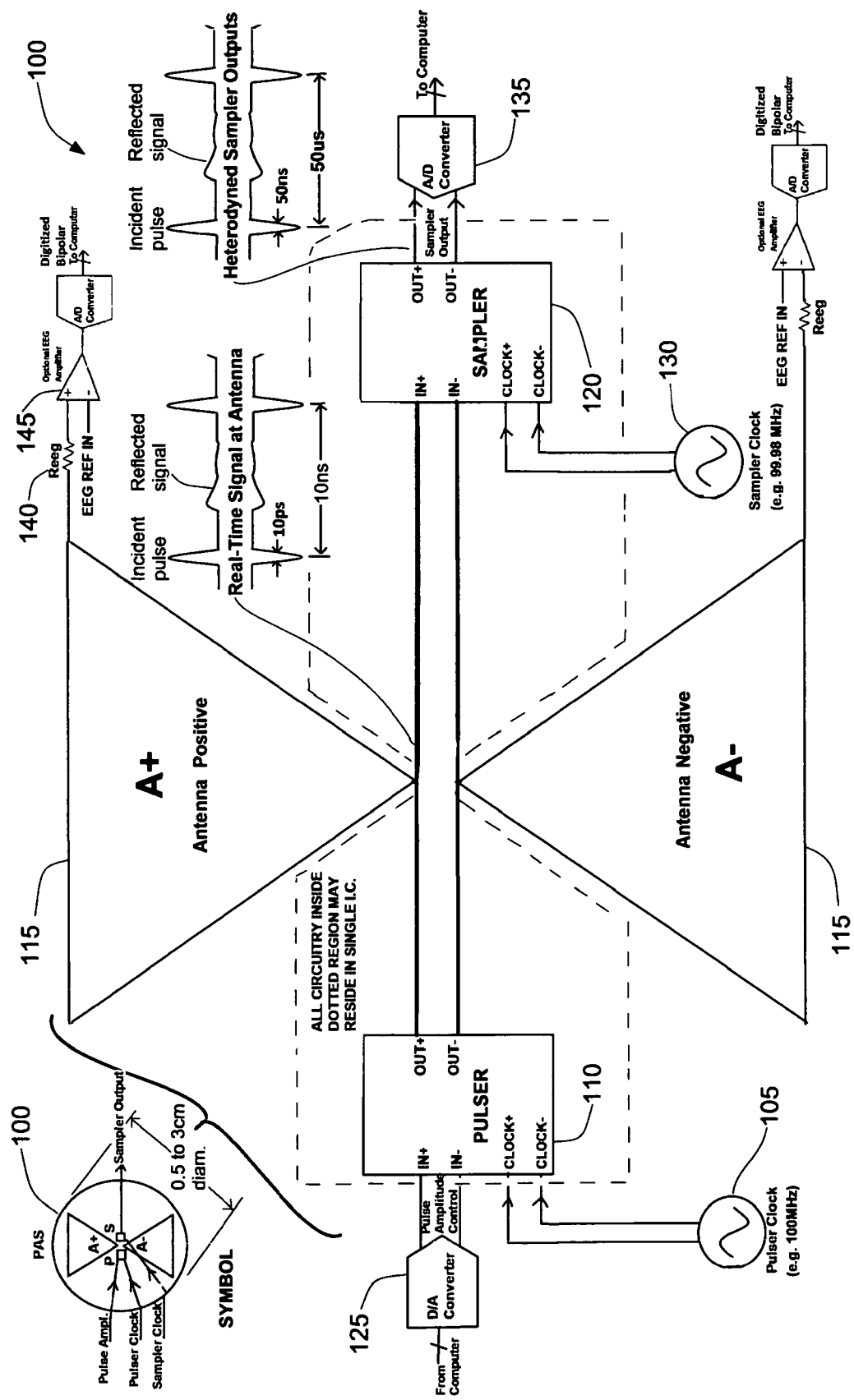
FIG. 1 is a circuit diagram of a pulser/sampler assembly and surrounding components according to an exemplary embodiment of the present invention.

The present invention provides a compact, sensitive, and low cost waveform-edge-based medical imaging system using one or more assemblies each containing an electrical pulse or square wave generator, an antenna or microwave probe, and an electrical sampler. The pulse generator, herein also termed a pulser, is located on an electrical circuit and generates an electrical pulse, meaning a short burst, of near-Gaussian shape in some embodiments. Pulses are fed to the antenna that in turn emits an electromagnetic wave whose amplitude envelope is essentially that of the electrical pulse's shape. In use, the antenna is oriented so the electromagnetic wave propagates into the surface of the body over a region of interest. The antenna also receives energy reflected from the body in response to its own pulses, and can further receive energy from pulses which propagated through the body from one or more other pulsers with their antennae. An electrical sampler, optionally located within the same electronic circuit as the pulser, records the output of the antenna over a brief time interval following each pulse, that interval referred to herein as the "receive aperture" or "sample aperture." The received energies are stored as a record of voltage as a function of time after the pulse and optionally first digitized before being stored. As used herein, an electrical or electronic circuit can include one or more integrated circuits, a discrete pulser made with, for example, a step-recovery diode, and a sampler made with an integrated circuit, etc. The present invention is commonly described herein in terms of a single integrated circuit, but a single integrated circuit is not essential and embodiments can be implemented with other electronic circuits in place thereof.

A microwave pulse generator, such as the pulser of U.S. Pat. No. 6,433,720, incorporated herein by reference in its entirety, when actuated repeatedly by an oscillator, such as Silicon Labs SI531 that is based on a conventional quartz crystal, hereinafter called a pulser clock, having a frequency F, produces a continuous series of pulses where each pulse is characterized by a narrow width, 3 to 1000 picoseconds in some embodiments, spaced sequentially in time, with a time interval of 1/F between pulses. Accordingly, the pulse train contains energy content at frequency multiples of F. For example, a pulser actuated by a 100 MHz clock will contain frequency content at DC, 100 MHz, 200 MHz, 300 MHz, 400 MHz, . . . , etc., to over 50 GHz, in some instances. In this way, using a low clock frequency, the pulser generates a broadband comb of microwave frequencies, enabling its utility in a microwave imager that sends narrow pulses into the body to reflect off of and/or pass through internal structures.

An imaging apparatus of the present invention can comprise one or more assemblies, each with a pulser capable of generating a series of pulses, typically at a rate between 1 million and 1 billion pulses per second, and each assembly with an electrical sampler that concurrently receives the resulting reflected and/or transmitted energy from multiple locations over the surface of the body in response to the pulses. The electrical samplers generally sample at the same rate as the pulsers, or at a slight frequency offset from the pulse rate. For example, a typical imager may have a pulse rate of 100 million pulses per second (MPPS), while the samplers may run at 99.98 million samples per second (MSPS), creating a heterodyned (downconverted) output waveform from the electrical sampler that repeats, in this example, 20,000 times per second. The output of each electrical sampler is generally filtered by a low-pass filter (LPF) and then converted to a digital output signal by an analog-to-digital converter (ADC). Advantageously, this heterodyned waveform contains content that varies at a low enough frequency to feed low-cost ADCs. The digitized output is sent to a processor, such as a digital signal processor (DSP), or other conventional hardware signal processing apparatus, that can average the digitized signals following multiple successive pulses, to enhance the SNR. It will be understood that references below to computer processing, such as where signals are sent to a computer to implement well known algorithms, also mean that the signals can be sent to a DSP or other microprocessor, or to a field programmable gate array (FPGA) or complex programmable logic device (CPLD) for such processing; a standalone computer is not a requirement.

The pulser and electrical sampler in some embodiments may be based on the circuitry in U.S. Pat. No. 6,433,720, and derivatives thereof, that place both the pulser and the electrical sampler on the same IC; these designs are advantageously small enough to be located directly at the feed points of each microwave antenna, creating a complete miniature RADAR front end. Furthermore, these samplers and pulsers, which are optionally fully-differential, have high impedance outputs and inputs, enabling better impedance matching and direct signal coupling to small microwave antennae, without the need for BALUNs and matching networks, significantly reducing ringing and signal loss between the antenna and the active pulser and electrical sampler.

Finally, the pulser/sampler circuitry of U.S. Pat. No. 6,433,720 allows the width, amplitude, and the polarity of the transmitted pulse as well as the width and polarity of the receive aperture (although the later capability is not required in the embodiments in this disclosure) all to be adjusted in real time, enabling multiple assemblies to be controlled by a single phase shifter 1110, and therefore to enable phased array radar techniques to be employed for imaging using directed beams. The adjustable pulse and sample aperture width further enables the ability to trade off frequency response for sensitivity. For example, a wide pulse and sample aperture can be used to image deep structures at the expense of sacrificing spatial resolution (selectivity). The combination of high pulse amplitude, low noise, pulse and aperture adjustability, small size, and low cost enables an assembly array having the density of assemblies required for portable medical microwave imaging systems. As each PAS assembly of an array connects its pulser and sampler directly to its antenna, it is noted that this configuration eliminates all microwave cabling from the array, so that all interconnect cables to and from the PAS assemblies carry only low frequencies and are therefore small, allowing a complete head imager to be built into a compact helmet.

The small size of the sampler and pulser circuitry allows both of these blocks to be contained on a single, small (under 4 square mm), low-cost IC, as shown in FIG. 1, enabling an array of hundreds of PAS assemblies to be built for lower cost than a single conventional VNA. Also, rather than the need, as with conventional systems, to switch an entire VNA between an array of antennae, the system of the present invention allows all PAS assemblies to be operated concurrently, yielding roughly three orders of magnitude better signal collection efficiency and enabling far more sensitive measurements, including the functional imaging, in real time, of very small changes in $E_r$ and transmissivity that are the result of dynamic changes in biological function in the body. Accordingly, embodiments of the present invention are able to resolve the depth at which reflectivity and conductivity changes occur in a human brain, thereby constituting a new functional imaging modality.

FIG. 1 illustrates an exemplary basic subsystem circuit of the present invention including a pulser/sampler/antenna (PAS) assembly 100. Assembly 100 is capable of both TDR and TDT, utilizing transitions from an external pulser clock source 105 to drive a clock input of a pulser 110 of the assembly 100. The OUT+ and OUT− terminals of the pulser 110 differentially drive electrical pulses into the two feed terminals of a balanced antenna 115. The same feed terminals are further connected to the IN+ and IN− inputs of a sampler 120. An optional conventional digital to analog converter (DAC) 125, intended to specify the amplitude of the pulses, drives the IN+ and IN− terminals of the pulser 110, which in turn generates a differential pulse at its OUT+ and OUT− terminals every time it receives a clock transition. The amplitude of an electrical pulse is proportional to the difference between IN+ and IN−. If IN+ amplitude is significantly greater than IN−, a positive-going pulse will be generated. If, however, the difference between IN+ and IN− is zero, then OUT+ and OUT− will have identical amplitude pulses, which if connected directly to a differencing means, such as a differential amplifier or BALUN, will yield no net energy to the antenna. Finally, if IN− is significantly greater than IN+, then a negative-going pulse will be generated. The Incident Pulse shown in the Real Time Signal at Antenna waveform graph in FIG. 1 is representative of the incident pulses generated by the pulser 110. It should be noted that although the invention is described with reference to differential circuits herein, the same principles can be applied to non-differential circuits with the paired terminals described herein replaced by a single terminal whose voltage is referenced to a an electrical "ground."

The resulting bipolar differential pulse signals from the differential output of the pulser 110 are fed to the antenna 115, which radiates a corresponding pulsed electromagnetic wavefront whose field intensity is essentially a replica of the driving pulse. This wavefront is radiated into a proximate body surface, and the resulting internal reflections are received back from the body, via the same antenna 115, as shown in FIGS. 2, 4, 5, 6, 7, 8, 9, 10, 11, 12, 13, 14 and 15. These reflections, depicted as "Reflected Signal" in the Real Time Signal at Antenna Waveform in FIG. 1, are sampled by the sampler 120. The sampler 120, which takes a sample every time it receives a clock transition from a sampler clock 130, outputs the sample, through an optional low-pass-filter (LPF)(not shown) to a conventional analog-to-digital converter (ADC) 135 whose output is fed to a computer, for processing as described below.

The sampler 120, pulser 110 and, optionally, the DAC 125, ADC 135 and clocks 105, 130 can be implemented in a single integrated circuit (IC) that may be installed directly at the antenna feed points, eliminating the need for controlled-impedance cables and significantly reducing ringing due to mismatch between the antenna impedance and that of the termination resistors in the sampler's input amplifier. Optionally, these components can be distributed over two or more ICs placed close together, for example, the pulser 110 could be implemented in one IC and the sampler 120 in a second IC.

The pulser 110 in the assembly 100 shown in FIG. 1 is driven by the pulser clock 105 at a frequency between 1 MHz and 1000 MHz (with 100 MHz being a typical representative value), in various embodiments, so as to produce 1 million to 1 billion pulses per second which are radiated into the location of the body being imaged. Other embodiments can employ frequencies both below and above this range. As the wavefront, or signal, of a pulse passes into the body, reflections occur at depths at which changes of dielectric permittivity $E_r$ (which are additionally frequency-dependent) are encountered, such as at the skin-to-skull boundary, and then at the skull-to-dura matter boundary, and then at the boundary between the dura-matter and the sub-arachnoid space (which contains cerebrospinal fluid), and then at the boundary between the end of the sub-arachnoid space and the surface of the brain, and then the boundary between the thin outer cortical grey brain matter and the deeper white brain matter, and so forth. Additionally, the velocity of the radiated pulsed wavefront changes as it traverses these various types of body tissue. Hence, the wavefront travels quickly through the skull bone, which has $E_r$ of approximately 15, while traveling at less than half of this velocity when traversing the cerebrospinal fluid, whose $E_r$ is approximately 65. Also, the time at which each reflection occurs is dependent on the depth at which the dielectric boundary occurs. Therefore, the echo reflected back to the antenna 115 occurs almost immediately from the boundary between skin and skull and much later (several nanoseconds later) for reflections from deep in the brain. Finally the amplitude of each echo is proportional to the change in $E_r$ between the shallower material and the deeper material at each boundary, and the time at which it reaches the antenna conveys the nature of the type of tissue and its depth. The amplitude of each echo is further affected by the degree of signal absorption (attenuation) as the pulsed wavefront traverses the shallower material in both the incident and reflected directions. The attenuation of tissue can also change as a result of changes in the functional activity of the tissue. The sampler 120 takes snapshots (recordings over a brief time interval, typically 3 to 1000 picoseconds) of the signal received by the antenna 115, and sends these to the ADC 135.

In various embodiments, the sampler 120 is driven by clock 130 at a frequency slightly lower than that of the pulser 110. For the example in FIG. 1, if the pulser clock 105 is 100 MHz, the sampler clock 130 would typically be slightly lower, for example 99.98 MHz, causing the sampler 120 to produce, at its output terminals, a downconverted waveform that repeats 20,000 times per second and constitutes a low-frequency heterodyned equivalent of the waveform, that is fed to ADC 135. Heterodyning enables very fast signals to be observed, using a sequence of samples, and reconstituted at a lower frequency for convenient measurement using a low-cost slow ADC. In the example of FIG. 1, this heterodyned output effectively portrays the 10 ns interval between the 100 MHz pulses as a 50 microsecond period (20,000 times as long). This signal, when plotted, is a rough one-dimensional image of the average permittivity of the tissues in front of (i.e. down-range from) the antenna, as a function of depth. As mentioned above, the sampler clock 130, in some embodiments, can also produce transitions with the same frequency as the pulser clock 105 but with a variable time offset added after each successive transition such that the delay after each successive transition increases. The sampler clock 130 can employ Vernier phase shifting, in some instances, to add the increasing time offset.

A simple method to generate a two-dimensional structural medical image involves scanning a PAS assembly 100 along a line over the surface of the body. The resulting density profiles can then be used to reconstruct the dielectric properties, and thus the tissue structures, along a plane inside the body. To generate a three-dimensional image, the PAS assembly 100 is scanned along multiple lines, in a raster fashion, traversing a two dimensional surface of the body. Conventional algorithms, such as reverse RADON transform, can be used to reconstruct the image, and algorithms, such as those used for synthetic aperture radar, are also used to effectively sharpen the radiated pattern of the antenna 115. Further, inverse scattering algorithms, as one skilled in the state of the art would be knowledgeable, may be used.

In cases in which the PAS assembly 100 is to be used for functional imaging of neural activity, it may be desirable to combine the changing information received from the PAS assembly 100 with that of a conventional EEG recording. While this could be achieved by attaching conventional EEG electrodes near each PAS assembly 100, doing so would occupy valuable scalp area, and could thus prevent the placement of PAS assemblies 100 in sufficiently close proximity to allow sufficient antenna array density for producing a high resolution functional image. It may therefore be desirable to have the two radiating surfaces of each antenna 115 serve the concurrent purpose of acting as EEG electrodes. This can be done by coupling each antenna half, through a resistor $R_{eeg}$ 140, to the positive input of a conventional differential EEG amplifier 145. The negative input terminal of the amplifier 145 can be connected to a conventional EEG reference electrode made of a material having the same metallic finish as that of the antenna half, and typically placed in a conventional EEG reference location such as the skin over the mastoid. This arrangement provides a unipolar EEG recording from the scalp under each antenna half.

If a bipolar EEG recording is desired between the scalp under one antenna half, and the scalp under a different antenna half (either on the same antenna 115 or a different antenna 115), the first terminal of the EEG amplifier is connected to the first antenna half, and the second antenna half is connected to the second terminal of the amplifier.

The purpose of resistor $R_{eeg}$ 140 is to prevent the EEG amplifier from causing undesirable loading of the antenna 115 at RF frequencies, while easily passing the low frequency (1 to 100 Hz) EEG signal content to the EEG amplifier. Finally, to enable such concurrent TDR/EEG, the antenna halves each need to be coupled to the sampler and pulser terminals through capacitors, of value typically between 100 pF and 0.1 uF, to prevent the low impedance of the pulser and/or sampler terminals from loading, and thereby attenuating, the EEG signals. The capacitors easily transfer the high frequency RF pulse energy and resulting received RF energy, while blocking the EEG signal.

The sampler 120 can optionally also be used to collect an EEG signal from each antenna half. This can be achieved by firmly electrically coupling the antenna half to the scalp, such as would be facilitated using electrode gel or another conductive substance or material.

While an image can be constructed using the above-described methods which use a single antenna that is mechanically scanned over the surface, this process is slow. In other embodiments, large numbers of PAS assemblies 100 are employed to significantly improve imaging speed and potential quality. Such imaging speed is essential for functional imaging, as the region of interest in the brain must be continuously re-imaged at a rate that is faster than the fastest changes in the neural or vascular activity of interest.

Figure 2:
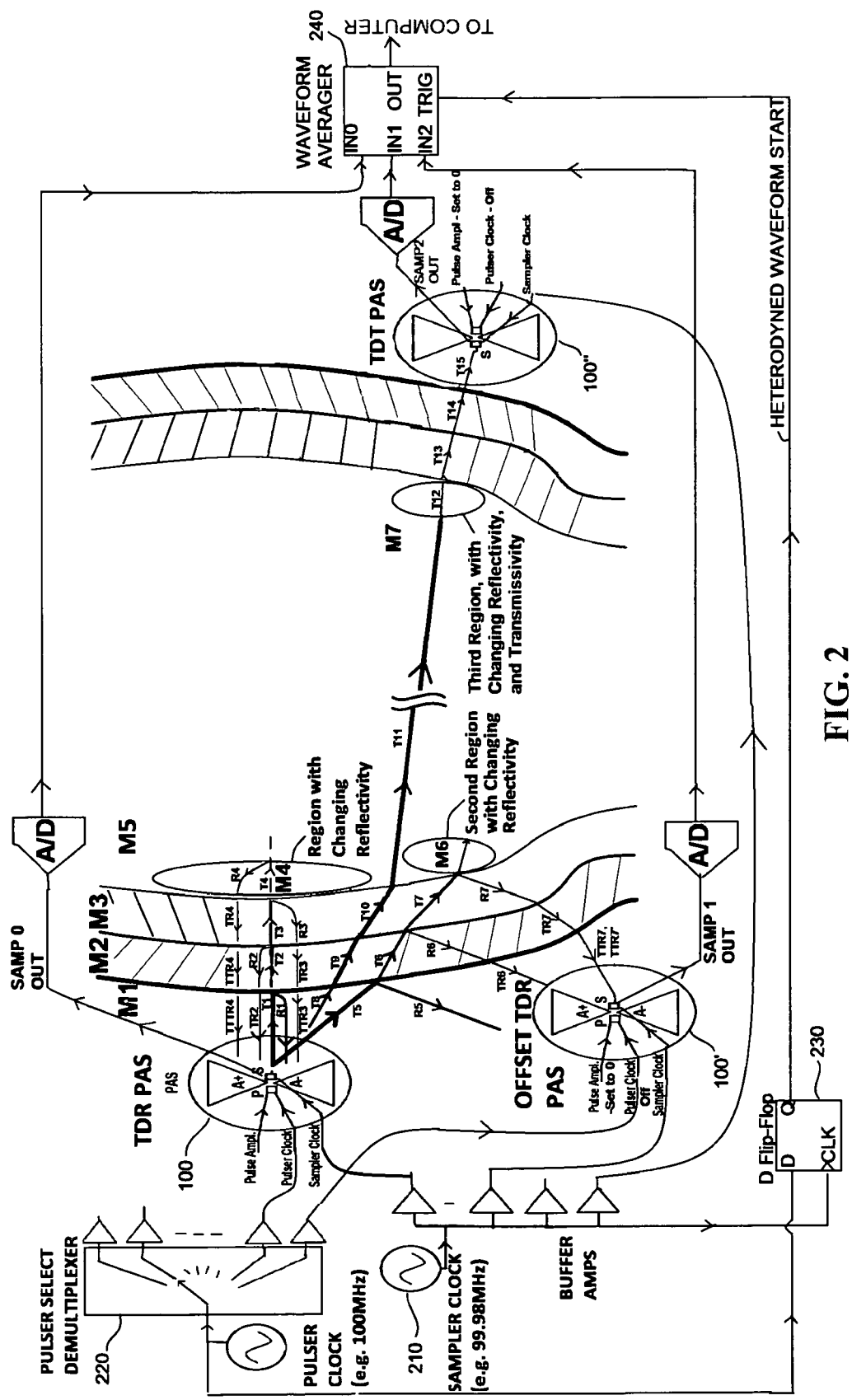
FIG. 2 is a schematic illustration of several pulser/sampler assemblies positioned around a head, according to an exemplary embodiment of the present invention.

A medical imager of the current invention is shown in FIG. 2, consisting of at least two PAS assemblies 100, each of which is either pressed into direct contact with the skin, or alternatively is immersed in a coupling fluid between the PAS assembly 100 and the skin, or is pressed against a bag full of gel or liquid that acts as a coupling medium between the antenna in the PAS assembly 100 and the skin. In the case of gel or liquid, this material, designated M1 in FIG. 2, is designed to have a relative permittivity $E_r$ of approximately that of the skin—typically approximately 50 (i.e. 50 times the permittivity, $E_0$ of free space). Or, in some cases the liquid may simply be water, which has a relative permittivity of 80. This allows efficient coupling between antenna 115 and body, enabling the use of a smaller antenna 115, as the effective wavelength is smaller due to the higher $E_r$. In some cases, the gel or liquid may contain a substance with not only high $E_r$, such as glycerin or water or a mixture thereof, but may also contain a substance with a magnetic permeability greater that of free space, further enabling the miniaturization of the antenna 115 in the PAS assembly 100 and allowing still tighter spacing between antennae 115 in neighboring PAS assemblies 100.

The TDR PAS 100 in FIG. 2 transmits pulses using its pulser 110, and receives the resulting reflected energy using the same antenna 115 that is also connected to its sampler 120. This sampler 120 then records the received signal over a sample aperture, and outputs the result to a conventional ADC 135 and computer for storage and/or analysis. The samplers 120 on both this TDR PAS assembly 100 and the OFFSET TDR PAS assembly 100' of FIG. 2 are each driven by a sampler clock 130 having the same frequency, for example, a frequency of 99.98 MHz. In the alternative, as shown in FIG. 2, a single sampler clock 210 can drive multiple samplers 120. However, only one of the PAS assemblies 100 is driven at a given time with a pulser clock 105—in this example, the TDR PAS assembly 100, is selected using the PULSER SELECT DEMULTIPLEXER 220 of FIG. 2.

The heterodyned outputs of the respective samplers in TDR PAS 100, OFFSET TDR PAS 100' and TDT PAS 100" each portray the 10 ns interval they sample between the 100 MHz pulses as a 50 microsecond period (20,000 times as long). These three outputs are each concurrently digitized by separate A/D converters, whose digital outputs are then fed to a waveform averager 240 of conventional design, which can be implemented using a DSP or FPGA for example. Such an averager generally requires a trigger to indicate the presence of each new waveform that needs to be averaged in with previously collected waveforms, which in this example occurs every 50 microseconds. This trigger can be provided by a D Flip-Flop 230 (such as On Semiconductor MC100EP51), whose clock input is fed from a buffered copy of the sampler clock 210 and whose D input is fed from a copy of the pulser clock. The resulting Q output of Flip-Flop 230 is a heterodyned 1-bit digital signal HETERODYNED WAVEFORM START in FIG. 2, whose rising edge occurs coincidentally with the beginning of the outputting of each new heterodyned analog waveform from the three samplers, and is used to trigger the summation of this new heterodyned waveform to the running sum of prior collected waveforms in the signal averager. This precise triggering enables each new waveform to be precisely registered with respect to the previously acquired waveform, ensuring that all sequentially summed (and thereby averaged after a simple later division by an integer equal to the number of summations) waveforms are time-aligned with respect to each other so they can be constructively averaged.

As the resulting wavefront from the pulser 110 in the TDR PAS assembly 100 propagates from the antenna 115, a portion labeled T1 transmits across M1 to the M1-to-M2 boundary where a portion thereof, labeled R1, is reflected back to the antenna 115 from that boundary. Here, M2 is used in this simplified example to represent the combined structure of skin, skull and dura matter, while M3 is used to represent CSF, and M4 represents a gray matter region whose dielectric properties are subject to change due to neural activity. M5 represents surrounding gray matter that is inactive at the time of the measurement, and therefore characterized by static dielectric properties.

While one portion of the energy represented by T1 is reflected back to the antenna 115 as R1, the remaining portion of the electromagnetic energy, denoted by T2, penetrates M2. A further portion, denoted as R2, of this energy later reflects off boundary M2-to-M3 across which there is a change in $E_r$, while the remainder of the energy, denoted T3, is transmitted into M3. A portion, denoted as R3, of this energy, reflects off the M3-to-M4 boundary, while the remainder, denoted T4, traverses M4 where a portion R4 is reflected and the remainder travels into M5—this portion is discussed later.

Figure 3:
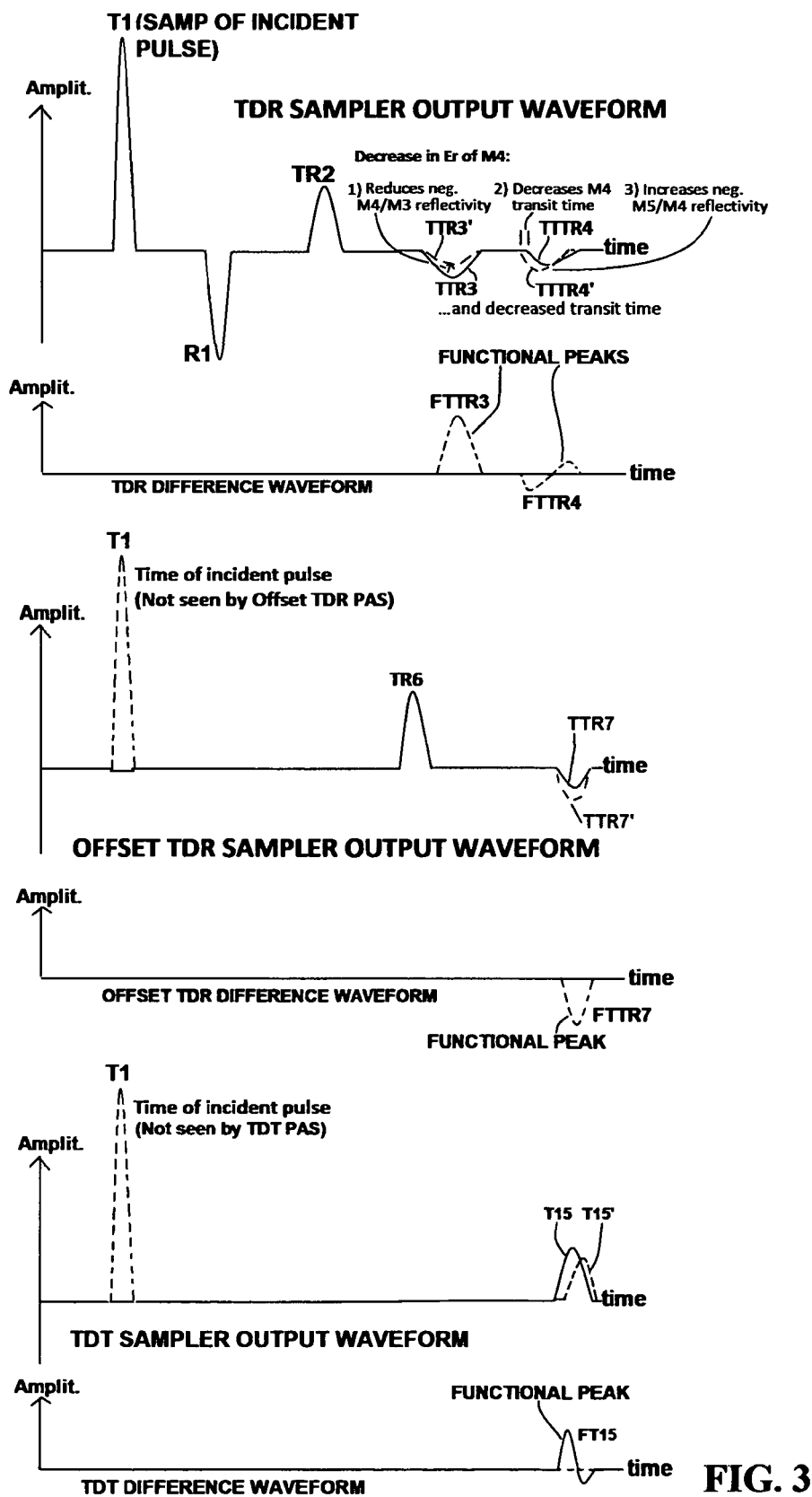
FIG. 3 shows various exemplary sampled waveforms that can be detected by pulser/sampler assemblies when positioned as in FIG. 2.

At each of the aforementioned boundaries, the energy that is reflected then propagates backwards toward the skin and some fraction eventually propagates out of the body and impinges on the same antenna 115 (in TDR PAS) from which the energy T1 was originally transmitted. Specifically, the energy in R2 traverses back into M1, where it is termed TR2. Similarly, the energy in R3 traverses back into M2, where it is termed TR3, and then further traverses back into M1 and back to the antenna 115, where it is termed TTR3. Finally, the energy in R4 traverses back into M3, where it is termed TR4, which then traverses back into M2, where it termed TTR4, which finally traverses back into M1 and the antenna 115, where it is termed TTTR4. The incident pulse T1 and then each of these respective pulse reflections R1, TR2, TTR3 and TTTR4 reaches the antenna at a successively later time, as shown in the plot "TDR SAMPLER OUTPUT WAVEFORM", in FIG. 3, which shows the sampler output, that is then digitized by the ADC 135.

In some imager embodiments, T1 may be clipped in amplitude if the transmitted pulse is of a sufficiently high amplitude to overload the input amp of the sampler 120 in the TDR PAS assembly 100. The clipping during receipt of the pulse is generally harmless, as the sampler 120 will recover from this temporary overload in time to receive the subsequent echoes. If, as in this example, material M2 has a higher $E_r$ than M1, then the reflection R1 will have a polarity opposite that of the incident pulse. Then, if material M3 has a lower dielectric constant than M2, the reflection TR2 reaching the antenna 115 will have a polarity that is the same as that of the incident pulse. Finally, in this example, the energy reflected at the M3-to-M4 boundary has an opposite polarity as the incident pulse, assuming M4 has a higher $E_r$ than M3.

It should be noted that the later echoes TR2, TTR3, TTTR4, etc., will have less amplitude since some energy is reflected and some energy transmitted at each successive boundary. Additionally, later reflection echoes are broadened, in part due to energy losses, which are worse at higher frequencies, as the wavefront propagates through body tissues. Additional broadening is due to dispersion—some frequency components of the pulse travel at different speeds than others, as the dielectric constants of tissues vary with frequency. The dispersion provides information that may be used as an aid to determining the level of functional activity in a region. By collecting TDR and/or TDT data from a large number of sequential pulses, and performing a Fourier transform to obtain the frequency spectral content of the returned data, and then further noting changes in the spectrum over time, the degree of the functional change and, more importantly, the nature or underlying mechanism for the functional change may be inferred and displayed.

A significant result of the high SNR of the circuitry of the present invention is its ability to detect very small changes in $E_r$, such as occur in regions of the human body in response to various factors such as changes in metabolite levels and neural swelling. In a TDR SAMPLER OUTPUT WAVEFORM plot in FIG. 3, the sampler 120 repeatedly detects a constant amplitude T1 of the incident pulse and reflections R1 and TR2, resulting from reflections between regions M1, M2 and M3 whose $E_r$ stays relatively constant over the time interval over which the apparatus is operating, such as over several minutes. However, in this example, region M4, which could represent a region in the cerebral cortex that is undergoing rapidly changing levels of activity, concurrently exhibits corresponding rapidly changing dielectric properties in response to changes in said underlying activity.

Although these changes are very slight, typically under a few percent, the result is that the reflection coefficient between static region M3 and changing region M4 changes, resulting in echo shape TTR3 seen by the sampler changing to shape TTR3' over time. A similar change occurs at the boundary between changing region M4 and relatively static region M5, but in opposite direction, as depicted by the morphing of echo amplitude TTTR4 to TTTR4'. Finally, the arrival time of TTTR4 will additionally vary due to the changing transit time through region M4. For example, if the dielectric permittivity $E_r$ of M4 increases, the velocity through M4 will slow, and hence echo TTTR4' will arrive later.

By capturing a received waveform at a fixed time, a baseline waveform can be established and stored. Subsequently acquired waveforms may then be subtracted from this baseline to yield, for example, the "TDR DIFFERENCE WAVEFORM" of FIG. 3, containing peaks TTR3 and TTTR4, which represent the changes in reflectivity due to changes in functional activity at region M4. The amplitude of TTR3 shows the relative dielectric permittivity $E_r$ of M4 as compared to M3, while the amplitude of TTTR4 shows the relative dielectric permittivity of M5 as compared to that of M4. Finally, the time of receipt of each peak is representative of the round trip path delay the pulse takes in reaching each dielectric tissue boundary, and changes in the arrival time of a given peak vs that of the next peak are inversely proportional to changes in dielectric permittivity, $E_r$ in the region between the tissue boundary causing the first peak and the tissue boundary causing the second peak. Hence, if peak TTTR4 moves leftward vs movement of earlier TTR3, it is because the dielectric permittivity, $E_r$, of region M4 is decreasing, therefore decreasing the transit time through region M4.

Although the amplitude and arrival time of reflection R1 does not itself indicate neural function, it is nevertheless useful, as it indicates the degree of coupling between the antenna 115 and skin. If R1 is low, it means that most of the transmitted energy is being efficiently coupled between antenna 115 and body, and will likely result in adequate amplitude of the later-received energy from deeper reflections. If R1 is high, due to lack of good antenna 115 coupling to the skin, the amplitude of R1 can be used as a normalization factor by the processing software, to correct for the losses due the poor coupling.

Returning to FIG. 2, the illustration also provides an example of an Offset TDR mode for detecting structural boundaries and/or functional changes in regions that are offset from the antennae 115. In this TDR mode, two similarly constructed PAS assemblies 100 are used, the aforementioned TDR PAS assembly 100 which both transmits a pulse and receives a series of echoes primarily from the region in front of the antenna 115, and a separate OFFSET TDR assembly 100' which does not transmit, but simply receives echoes from the regions in which the pulse from the TDR assembly 100 reflects to reach the OFFSET TDR assembly 100'. By combining the acquired signals from one or more TDR PAS assemblies 100 assemblies with the acquired signals from one or more OFFSET TDR PAS assemblies 100', a two or three-dimensional image may be reconstructed. This image contains reflection data that is largely from internal structures directly in front of each antenna 115, as well as from internal structures of different depths, that all reside laterally between the two antennae 115.

For example, structural details or functional changes in region M4 are primarily detected by the TDR PAS assembly 100 that is directly over that region, while structural details or functional changes in region M6, which is laterally located between the TDR PAS assembly 100 and the OFFSET TDR PAS assembly 100' are largely detected by the offset TDR assembly 100'. As depicted in FIG. 2, the signal from the TDR assembly 100 follows the path T5, and then T6 when it traverses layer M2, and then T7 when it traverses layer M3 and finally impinges on functional region M6. When reflecting off of the M3 to M6 boundary, the reflected angle is the same as the angle of incidence, following path R7 and then TR7 and TTR7, to the OFFSET TDR PAS assembly 100'. In the event that M6's $E_r$ dynamically changes, the signal TTR7 that reaches the OFFSET TDR PAS assembly 100' will vary over time, as shown in the timing diagram "Offset TDR Sampler Output Waveform" in FIG. 3.

By capturing this waveform at a fixed time, another baseline waveform can be established and stored. Subsequent waveforms acquired by OFFSET TDR PAS assembly 100' may then be subtracted from this baseline, yielding the waveform labeled as "OFFSET TDR DIFFERENCE WAVEFORM" containing peak FTTR7, which represents the changes in reflectivity due to functional changes in region M6.

Returning to FIG. 2, the illustration also provides an example of a TDT mode for detecting structural boundaries and/or functional changes in regions that are located along a path between transmit and receive antennae 115. Here, two similarly constructed PAS assemblies 100 are used, the aforementioned TDR PAS assembly 100 which both transmits a pulse and optionally receives echoes primarily from the region in front of the antenna 115, and the separate TDT PAS assembly 100'' which does not transmit, but simply receives transmitted energy that traverses the regions in which the pulse from the TDR PAS assembly 100 travels, such as through the tissue in functional region M7, to reach a TDT PAS assembly 100".

By combining the acquired signals from one or more TDR or OFFSET TDR assemblies 100, 100' with the acquired signals from one or more TDT PAS assemblies 100", a two or three-dimensional image can be reconstructed. This image contains reflection and transmission data that is largely from internal structures directly in front of each antenna 115, as well as from internal structures of different depths, that all reside along a path between the two antennae 115. For example, structural details or functional changes in region M7 could be primarily detected by the TDT PAS assembly 100", if it were instead to be run in TDR mode, as it is directly over that region, while structural details or functional changes in region M6, which is laterally located between the TDR PAS assembly 100' and the TDT PAS assembly 100" are largely detected by the OFFSET TDT PAS assembly 100'.

As depicted in FIG. 2, the signal from the TDR PAS assembly 100 follows the path T8, and then T9 when it traverses layer M2, and then T10 when it traverses layer M3, and then T11 when it traverses white matter region M5 and finally impinges on functional region M7, travelling through M7 along Path T12 where its velocity and attenuation is affected, in real time, by changes in functional activity within region M7. After emanating from M7, it travels to the TDT PAS assembly 100" via paths T13 and T14. In the event that the $E_r$ or conductivity of region M7 dynamically changes, the signal T15 that reaches the TDT PAS assembly 100" will change over time, as shown in the timing diagram "TDT Sampler Output Waveform" in FIG. 3. By capturing this waveform at a fixed time, another baseline waveform can be established and stored. Subsequent waveforms acquired with the TDT PAS assembly 100" are then repeatedly subtracted from this baseline, yielding the waveform labeled as "TDT DIFFERENCE WAVEFORM" containing peak FT15, which is the difference between the signal T15' and T15 (shown in the TDT Sampler Output Waveform above), which represents the changes in reflectivity due to functional changes in region M7.

The above-described capability for functional neuroimaging as well as real-time imaging of vascular wall motion has been experimentally verified by the inventors, when conducting experiments in which reflectivity was plotted versus depth and antenna position over the left and right frontal cortexes while a subject was presented with changing visual stimuli and when performing mental or motor tasks. While this experiment was performed using just two antennae 115, it nevertheless demonstrates the capability of detecting changes in reflectivity over both the depth axis, and the lateral axis along the surface, constituting a rudimentary two-dimensional image. The addition of larger numbers of distributed PAS elements and appropriate signal processing of the returned signals can provide three dimensional images that show changes in reflectivity in real time in response to localized changes in brain activity. Imagers of the present invention thereby use microwave pulses to provide structural and functional images.

Figure 4:
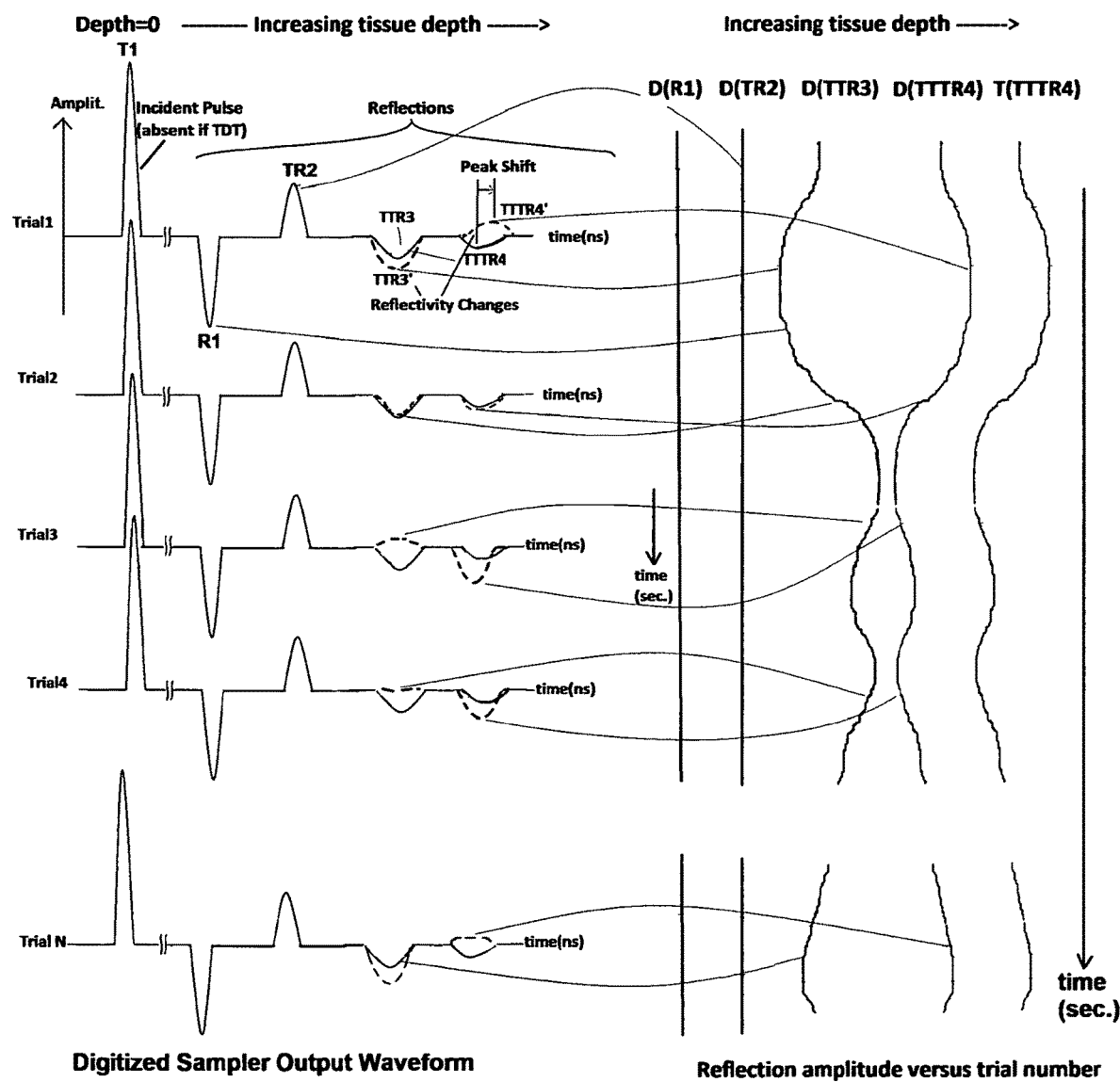
FIG. 4 shows an exemplary series of sampled waveforms from successive pulses impinging on tissue undergoing a change, according to an exemplary embodiment of the present invention.

FIG. 4 shows a series of repeated reflectivity waveforms (left) from tissue boundaries of interest at various depths changing over time in response to changes in functional activity with depth. For example, the TDR waveforms can be collected every few milliseconds—in this case the waveform in Trial 1 in FIG. 4 being acquired initially, the waveform in Trial 2 being acquired 5 ms later, the waveform in Trial 3 being recorded 10 milliseconds after the start, etc, until many seconds or even minutes or hours elapse, creating a chart recording of neural activity vs depth. Note that many of the portions of each waveform, such as R1 and TR2 from FIG. 2, are unchanged from trial to trial, but others such as the amplitudes of TTR3', TTR4', and the position of TTR4' change over time, due to changing dielectric properties of tissue in functionally active region M4 in response to changing metabolic activities or mechanical motion in the tissues on either side of each tissue boundary.

For each of those times corresponding to depths in which reflectivity changes, a second plot can be made, such as shown in the right of FIG. 4 showing how the reflectivity, and therefore the underlying metabolic activity, varies as a function of time. For example, the reflections at R1 and TR2 may correspond to the reflection of the incident pulse at T1 as the pulse first reflects off the skull and then off the skull-to-cerebrospinal fluid (CSF) boundary portrayed earlier in FIG. 2. These reflections may not change over time, as metabolism is relatively constant in these tissues. If the intensity of the signals at these times is plotted over time, the result will be a straight line, as indicated by the plot lines D(R1) and D(TR2). However, at time TTR3 which occurs later due to the pulse interacting with tissues at greater depth, the signal may correspond to the reflection from the surface of the brain, whose $E_r$ may rapidly change in response to changes in mental activity. So, the amplitude of waveform D(TTR3) may fluctuate over time, giving an indication of changing mental activity at the depth of the surface of the brain. Since not all of the pulse energy reflects off the tissue at D(TTR3), but propagates deeper into brain, a later reflection, such as that seen at time TTR4, may indicate changes in $E_r$ at this increased depth. If the signal at time TTR4 is plotted over many trials, it will yield the plot shown as D(TTR4), showing metabolic changes deeper in the brain. Similarly, the arrival time at the M4-to-M5 boundary will change in response to changing dielectric and mechanical properties of the active brain tissue at region M4. In this way, a series of layered plots can be made, showing dielectric changes at, for example, 256 different depths.

Figure 5:
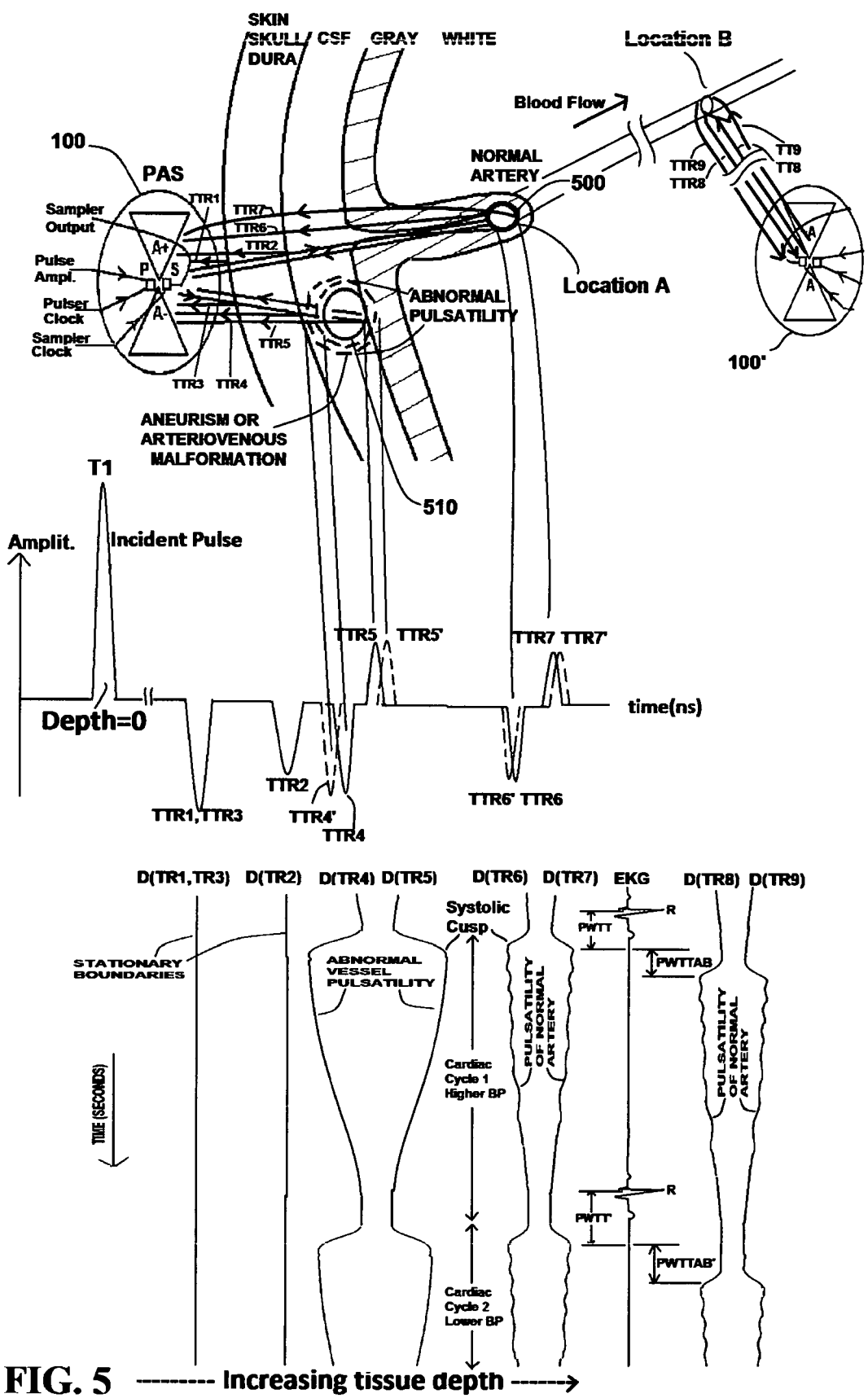
FIG. 5 shows two pulser/sampler assemblies imaging the motions of the walls of an exemplary healthy blood vessel and an exemplary diseased blood vessel.

In addition to detecting neural activity, embodiments of the present invention are capable of detecting arterial pulsation and CSF motion by virtue of the dynamic effects these phenomena have on the locations of vessel walls or tissue boundaries. FIG. 5 shows a PAS assembly 100 emitting pulses, and detecting the return echoes from two blood vessels, a first healthy artery 500, with a thick wall, and hence a small amount of expansion and contraction during systole and diastole, respectively. The second vascular structure 510 contains an aneurism or the draining veins of an arteriovenous (AV) malformation, and the wall is thinned in this region, resulting in increased amplitude of pulsatility in response to the heartbeat.

The pulse emitted from the antenna 115, with its broad radiating pattern, takes several paths as it enters the head. The pulse as it travels toward the normal artery 500 first hits the skin where some energy is reflected, as shown by return path TTR1. The unreflected portion continues through the skin, skull, and dura (shown as one composite element, for simplicity), until it reaches the subarachnoid space containing CSF. The significant discontinuity between the $E_r$ of the skull (approximately 20) and the CSF-filled subarachnoid space, whose $E_r$ is approximately 70, results in a reflection, along path TTR2. The remaining unreflected signal travels to the proximal wall (the first arterial wall the transmitted pulse encounters as it travels from the antenna) of the normal artery 500, where it reflects back to the antenna 115 along path TTR6 which is shortened as the artery 500 expands during systole. The remaining un-reflected signal travels through the blood in the artery 500 to the distal wall (the later arterial wall encountered by the pulse), where it reflects back to the antenna 115 along path TTR7, which expands during systole, delaying the receipt of the echo to time TTR7' in the middle diagram of FIG. 5. The reflected pulses from path TTR1 have the same delay on each trip, as they are reflections from stationary boundaries. However, there is a slight variation in the peak times of echo signals TTR6 and TTR6' as the heart beats. Similarly, the time of arrival varies slightly between TTR7 and TTR7', resulting in a spreading and contracting of the time between TTR6' and TTR7' in response to the narrowing and expanding of the normal artery 500.

In a similar manner, the pulse, as it travels toward the abnormal artery 510, first hits the skin, where some of it is reflected, as shown by return path TTR3. The un-reflected portion then continues through the skin and skull and dura until it hits the subarachnoid space where it almost immediately impinges on the proximal wall of the abnormal artery 510, where it reflects back to the antenna 115 along path TTR4 resulting in an echo pulse at position TTR4 in the waveform plot in the middle of FIG. 5. This echo position is shortened to TTR4' as the thin-walled abnormal artery 510 expands significantly during systole. The remaining un-reflected signal travels through the blood in the artery 510 to the distal wall, where it reflects back to the antenna 115 along path TTR5, yielding echo signal TTR5, which timeshifts significantly to later position TTR5' during systole.

There is an abnormally large variation between the lengths of paths producing echoes TTR4 and TTR4' resulting in a varying position of these peaks as the heart beats. Similarly, the time of arrival varies greatly between TTR5 and TTR5', resulting in a spreading and contracting of the time between TTR4' and TTR5' in response to the severe narrowing and expanding of the abnormal artery 510. The positions of all reflected peaks are plotted sequentially over time (i.e. every few milliseconds) in the bottom graph in FIG. 5, as the heart beats. Two successive heartbeats are plotted in this example—the first beat having a higher pressure than the second. The peaks due to stationary reflections D(TR1) and D(TR3) remain constant in arrival time, resulting in a flat line plotted over time, while the plots D(TR4) and D(TR5) show a severe fluctuation, in opposing directions, as their respective wall positions move closer and further from the antenna 115 as the weakened artery 510 expands and contracts heavily with each heartbeat. Conversely, the plots D(TR6) and D(TR7) show only mild fluctuations, also in opposing directions, as the normal artery 500 only modestly pulsates.

By sliding a single PAS 100 element over a suitably large area on the surface of the head, or alternatively using an array of PAS 100 elements spaced over the scalp, it is possible with the apparatus of the present invention to detect regions of abnormally high pulsatility amplitude that may be caused by such abnormalities as aneurisms and AV malformations. In the case of an AV malformation, the draining veins are directly exposed to arterial flow, resulting in an abnormally high degree of pulsatility in their thin walls, which were not intended to handle the much higher arterial pressures. By screening for such circulatory defects, it may be possible to plan a surgical intervention to prevent a potentially fatal vessel rupture.

An additional capability of the present invention is to infer approximate blood pressure (BP) by combining the invention's ability to dynamically image vessel wall motion, with the use of conventional pressure wave transit time (PWTT) algorithms for measuring blood pressure changes. The PWTT method infers BP by measuring the time that elapses between the time of the R wave of a conventional EKG, and the time at which the pulsation occurs at a known position along an artery of known location in the body. The R wave is the highest amplitude peak in the EKG, and it immediately precedes ventricular contraction and is thus a convenient predictor of the beginning of both left-side and right-side ventricular contraction and the resulting ejection of blood from both sides of the heart. The time it takes for this blood to later reach a point downstream, such as in an artery in the brain or lungs, or the capillary beds in the fingertips is inversely proportional to blood pressure. A higher pressure results in a stiffer, less elastic, arterial wall and a resulting faster propagation velocity along the arterial paths, and therefore a reduced time between EKG measurement of the R wave and the subsequent microwave-pulse measured mechanical wall pulsation at the point of measurement downstream along the arterial paths. In conventional uses of the PWTT technique, the delay time between the EKG R wave and the capillary beds in a finger are typically used, but accuracy suffers due to positional changes in the arm from measurement to measurement and reduced peripheral circulation in older patients and those with vascular disease.

The apparatus of the present invention can provide improved accuracy by virtue of its ability to image arteries in the more centrally located brain arteries. The apparatus of the present invention is first used to image the structure and location of a segment of a known artery, such as an internal carotid artery. Then, based on the ability of the apparatus to dynamically measure vessel wall motion, the time at which the vessel walls begin to expand (pulse) outwards can be measured for each heartbeat, as shown in waveforms D(TR6) and D(TR7). Using the time thus measured, blood pressure can be inferred, as both the rise time and the time the expansion of the vessel occurs after the R wave are shortened with increasing blood pressure in the vessel. In the example in FIG. 5, the first heartbeat is more forceful than the second, resulting in a higher BP for that cycle, and a shorter transit time PWTT. The second heartbeat is less forceful, resulting in a lower BP and a longer transit time PWTT'. Hence the ability of the invention to infer BP is demonstrated.

The apparatus of the present invention can further measure BP, without the requirement of the use of EKG, by simply measuring the time between the pulse wave measured at a first location A along a normal artery 500 and the later occurring pulse wave at a second location B further downstream on the same artery 500 or of a separate artery with a longer path length from the heart than that of the first artery, using a second PAS assembly 100'. As pressure in the artery increases, the transit time between the peak of the arterial pulsation at the first location and that at the second location decreases, and hence the pressure can be inferred by measuring the time of receipt of the changes in position of the echoes from the pulses that reflect off the walls of these two locations. The measurement of pulsatility at said first location is typically done using a first PAS 100, or first group of PAS assemblies, while the measurement of pulsatility at said second location is done using a second PAS 100' or second group of PAS assemblies. In the example of FIG. 5, the forward and return paths between the second PAS 100' and the proximal arterial wall at location B are labeled TT8 and TTR8, respectively, and the forward and return paths between the second PAS 100' and the distal arterial wall at location B are labeled TT9 and TTR9. The changes in echo arrival times at PAS 100' in response to arterial pulsation at Location B are plotted as D(TR8) and D(TR9) respectively. As the blood travels from Location A to Location B, the transit time between the Location A pulse waves D(TR6) and D(TR7) and the Location B pulse waves D(TR8) and D(TR9) depends upon blood pressure. For the higher pressure cycle, the transit time PWTTAB is shorter than the transit time PWTTAB' for the subsequent, and lower pressure, cycle.

The ability to measure the time of pulsation of two separate arterial locations constitutes an advance in non-invasive BP measurement, as it can be used to infer pressure in locations within the body that are not available at the surface of the body, such as the pressures in the pulmonary arterial system. Also, the PWTT technique is able to measure BP on a beat-to-beat basis, rather than requiring a long series of heartbeats, such as is the case with conventional cuff-based BP measurement techniques.

It should be noted that the blood pressure measured by observing arteries within the brain yields an approximation of the standard blood pressure produced by the left side of the heart. The present invention can also be used to non-invasively measure the right side blood pressure, presently performed by invasive techniques. Right side blood pressure can be an important measurement, but a somewhat risky clinical procedure, that is sometimes needed when monitoring critically ill patients in the intensive care unit (ICU). Right side blood pressure can be measured according to the present invention, for example, by measuring a transit time difference between either two diverse points along a pulmonary artery, or alternatively the time between the R wave (which causes both right and left sides of the heart to beat almost concurrently in a healthy person), and the microwave-measured pulse wave along a single point along a pulmonary artery. For right side blood pressure measurements the array of microwave pulser/sampler assemblies are disposed on the surface of the chest, over either two diverse locations along a pulmonary artery, or over two separate arteries in the lung having different distance from the heart. Additionally, two separate clusters of pulser/sampler assemblies can be arranged with one over the left chest and one over the right chest, in order to measure left and right lung pulmonary pressures which are sometimes slightly different in certain disease states.

In both the conventional PWTT technique using pulsation of capillary beds in the finger, and the PWTT technique using the current invention to measure arterial movement, it is necessary to calibrate the unit for a given person by correlating the pressure wave transit times measured against conventional (e.g. cuff-based) sphygmomanometer readings.

Figure 6:
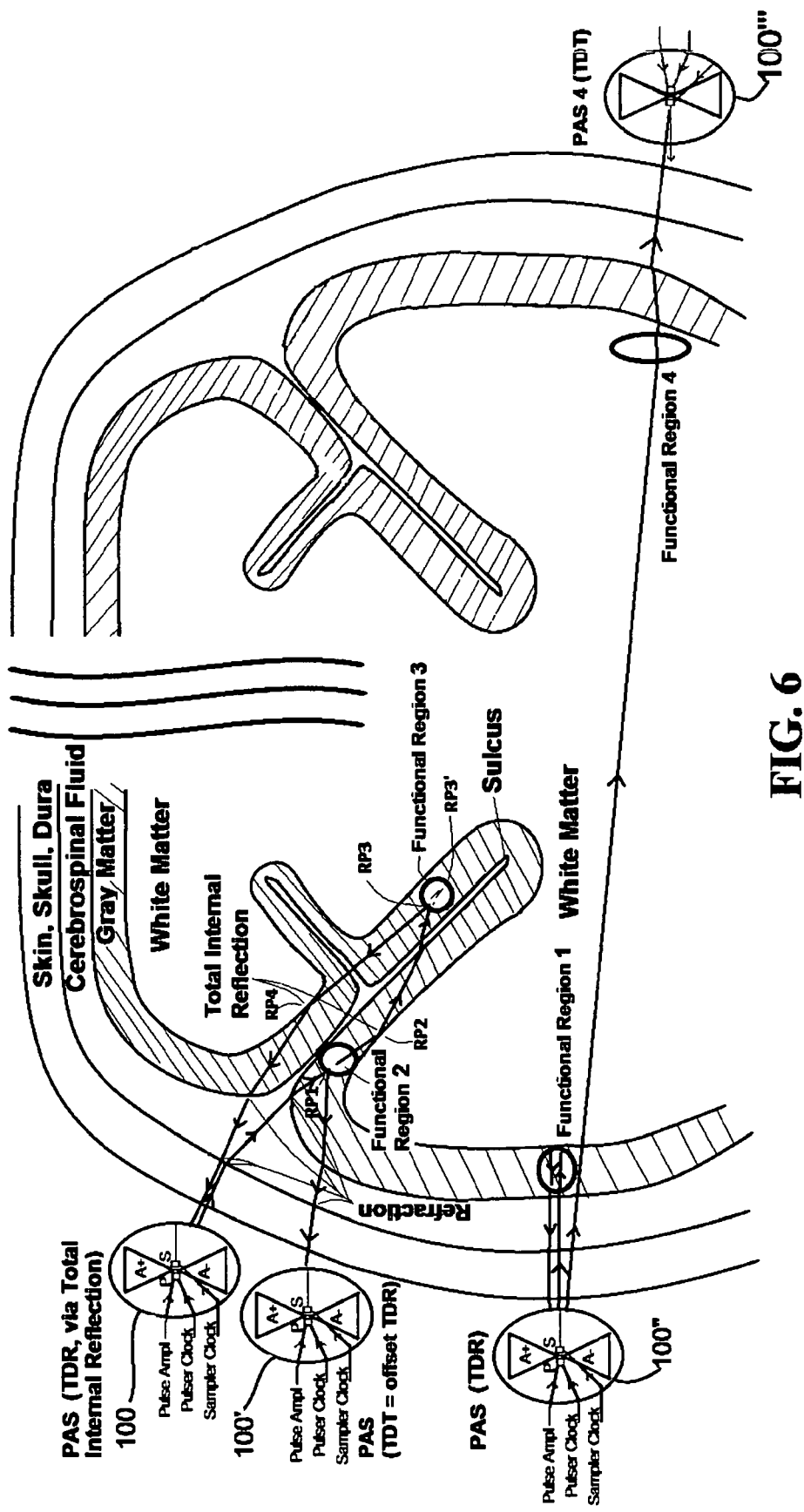
FIG. 6 is a schematic illustration of several pulser/sampler assemblies positioned around a head to image various features according to exemplary embodiments of the present invention.

The present invention is particularly capable of imaging changes due to neural activity and blood flow in the cortex, which is the outermost, gray matter, blanket of the brain. The gray matter has convolutions composed of gyri and sulci. Gyri are the outer folds, closest to the skull, while sulci are inwardly protruding folds of cortical tissue, as illustrated in FIG. 6. Measuring changes in dielectric reflectivity in a gyrus, as is being done by PAS 100" for Functional Region 1 in FIG. 6, is straightforward, as such gyri lie near the skull.

The present invention is additionally capable of inferring activity in cortical sulci, by virtue of the fact that a wave may be channeled through a sulcus due to internal reflection, by virtue of the gray matter having an $E_r$ of approximately 50, while the white matter has an $E_r$ of approximately 38 at the frequencies used. In fact, for shallow angles the well-known phenomenon of total internal reflection results in a waveguide being formed in the gray matter of many of the sulci, with a critical angle of approximately 60 degrees from a perpendicular to the gray/white matter boundary. In the example of FIG. 6, PAS assembly 100 launches a pulse wave into a sulcus at a shallow angle, where some of its energy is reflected off reflection point RP1 on Functional Region 2 and to adjacent PAS assembly 100'. The degree of dielectric change between Functional Region 2 and the surrounding gray matter will cause a time-varying change in reflectivity that is related to neural or vascular activity at Functional Region 2. The energy that was not reflected off Functional Region 2, but instead traversed it then bounces off location RP2 on the internal wall of the sulcus, after which it propagates to, and reflects off of location RP3 of Functional Region 3, then reflects off the sulcal wall at RP4, to be received by antenna 115 of PAS assembly 100. Some of the energy that does not reflect off RP3 may traverse Functional Region 3 and instead reflect off of RP3', yielding information as to the dielectric changes at the distal portion of Functional Region 3. In this way, as the pulse propagates through, or reflects off of, each functional region, the arrival time and amplitude of the returning signals are dynamically changed as the $E_r$ in the functional region changes in response to its neural activity or vascular pulsation.

Functional activity may be detected and imaged by either TDR, offset TDR, or TDT techniques. For example, in Functional Region 4 of FIG. 6, a pulse transmitted by PAS assembly 100" is not only used to image Functional Region 1 by means of TDR by means of changes of reflectivity, but is also used to image Functional Region 4 by TDT, enabled by the receipt of the transmitted energy reaching PAS assembly 100', at the far side of Functional Region 4. Changes in functional activity in Functional Region 4 cause changes in dielectric permittivity, which in turn cause changes in reflection of the incident pulse into the region, as well as causing changes in transmission velocity through the region, thereby advancing or delaying the receipt of the signal at PAS assembly 100'''. Finally, functional changes can cause changes in conductivity in Functional Region 4, which can be seen as changes in attenuation through the region and received on the other side by PAS assembly 100'. Changes in permittivity and conductivity can also be frequency-dependent, with lower frequency components of the waveform signal traveling at one speed, while higher frequency components travel at a different velocity.

The change in reflectivity and transmission velocity in neural tissue in response to functional changes is very faint, and hence the changes in amplitude and arrival times for the return echoes or transmitted signals due to dielectric changes is small compared to similar arrival changes due to artifactual forces, such as antenna motion, muscle movement, and vascular pulsation. For this reason, it is desirable to be able to detect such undesired artifact-caused arrival time changes, and account for them. This can be done by periodically detecting, and normalizing to, the echo arrival time of a dielectric boundary within the head that maintains a constant distance from the dielectric boundary in the functional region of interest.

Figure 7:
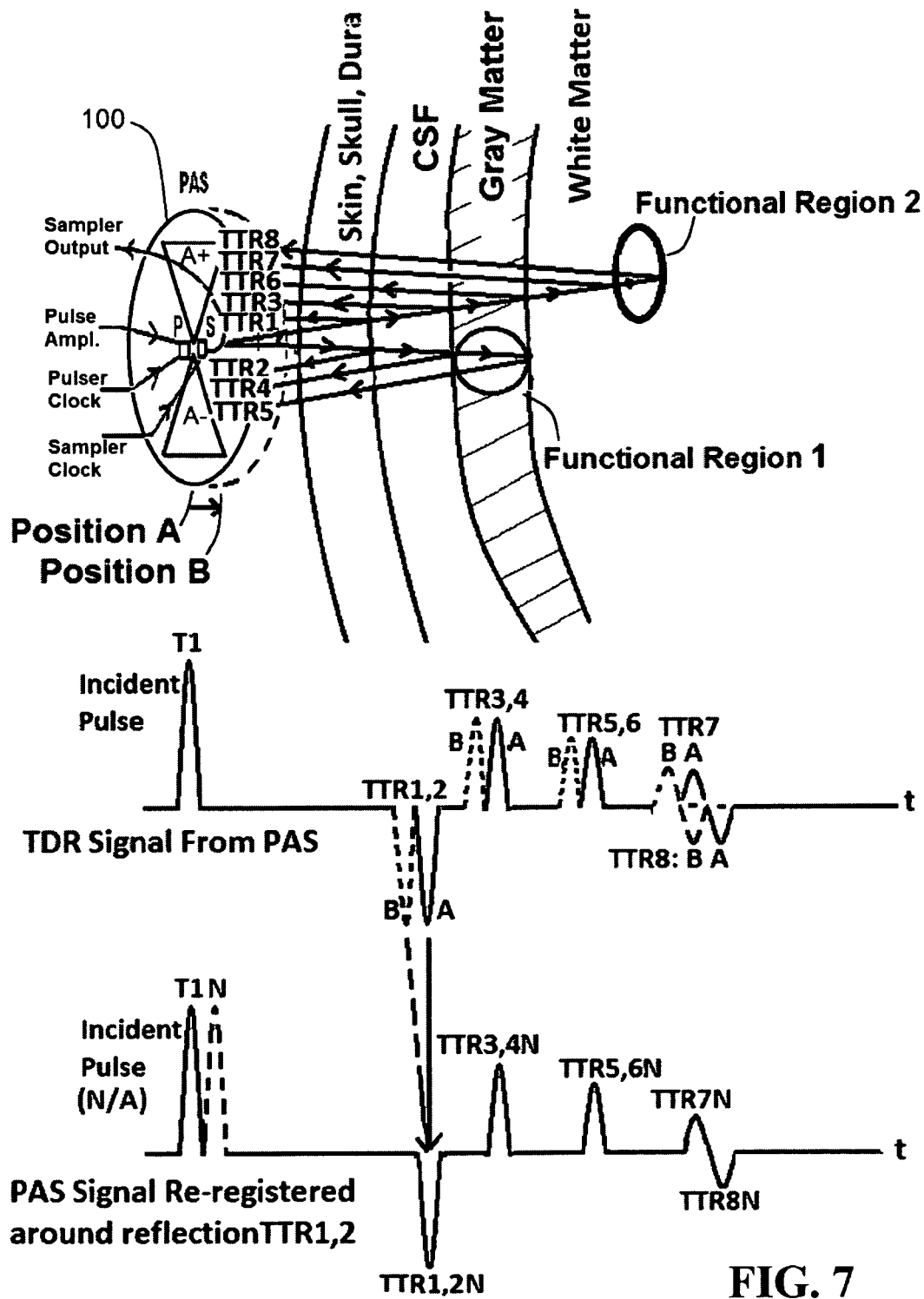
FIG. 7 shows a pulser/sampler assembly positioned proximate to a head and imaging features while moving relative to the head to illustrate how such motions can be compensated for, according to an exemplary embodiment of the present invention.

The example in FIG. 7 illustrates such a method for compensation for undesirable motion of the PAS assembly 100 with respect to the head. Position A is the desired PAS assembly 100 position, while Position B is a temporary undesired position due to bumping the PAS assembly 100 so it is closer to the head, resulting in an artifact in which all echoes are translated so they momentarily appear earlier in time, thereby potentially appearing as changes in dielectric properties in the brain. Fortunately, it is possible to compensate for such a motion-induced artifact by noting its effect on a known, and easily identified, dielectric boundary in the head, such as the dura-to-CSF boundary shown in the example in FIG. 7. The incident pulse from the PAS assembly 100 is seen at time T1 regardless of the position of the PAS assembly 100, and when the PAS assembly 100 is at its normal undisturbed position the reflection from the dura-to-CSF boundary is normally seen at time TTR1-A (and also TTR2-A for the alternate path in this example). The later reflection from the beginning of functional region 1 is seen at time TTR4-A, and that from the end of functional region 1 is seen at time TTR5-A. Similarly, the reflections from the beginning and end, respectively, of functional region 2 are seen at time TTR7-A and TTR8-A.

However, when the PAS assembly 100 is bumped to disturbed position B the reflection from the dura-to-CSF boundary moves to time TTR1-B (and also TTR2-B for the alternate path in this example). The later reflection from the beginning of functional region 1 moves to time TTR4-B, and that from the end of functional region 1 is seen at time TTR5-B. Similarly, the reflections from the beginning and end, respectively, of functional region 2 are seen at time TTR7-B and TTR8-B.

Fortunately, despite the PAS assembly 100 being mechanically disturbed, the distances between the dura-to-CSF boundary and all points in the brain remained constant, and the delays in pulse travel times between this boundary and said points correspondingly remained constant. Hence, motion-induced errors can be corrected for by simply subtracting the signal arrival times for these later points from the arrival time from the dura-CSF boundary. In other words, the arrival time of the reflection from the dura-CSF boundary serves as a baseline, and changes in that arrival time can thereafter be added or subtracted from the arrival times of other peaks to correct for such movements. Hence, in the processed data represented by plot "PAS Signal Re-registered around reflection TTR1,2" in FIG. 7, all echoes are stable, eliminating the undesired motion artifacts from the faint differences in arrival times due to actual neural or vascular activity. It will be apparent that alternate boundaries, such as the CSF-to-gray matter boundary, could be chosen instead as registration points.

More importantly, a boundary of a known-functionally-active region can be used as the registration point, from which a later boundary in the same region, or even a boundary in a different functional region, could be subtracted, to more precisely study the relationship between functional changes in different areas of the brain. This concept can be extended to where hundreds of differential registration points are used as baselines for hundreds or even thousands of other functional boundaries enabling a robust and powerful instrument for studying neural function, or other parameters such as differential pulsation among a variety of vascular structures, or relationships between functionality in multiple diverse neural regions.

While the method illustrated in FIG. 7 will compensate for motion-induced artifacts caused by linear displacements between the PAS assembly 100 and head surface, it will not compensate for lateral translation or angular changes in orientation (canting) of the antenna 115. However, the method can be extended to all three dimensions and three rotational axes. For example, using conventional beam steering and image reconstruction techniques, three dimensional structural images of any tissue boundary may be made, for the purposes of providing a reference surface for which the echo arrival times as a function of x,y,z coordinates on the surface is thus determined as a set of baseline values. Then, the arrival times of echoes that are downstream (later-arriving) in subsequent real time images are subtracted from these baseline echo arrival times, for the purposes of cancelling out artifacts that are caused by complex motions of the PAS assembly 100 relative to the head. It will also be apparent that this methodology for "locking onto" and establishing a boundary as a reference surface, can be extended to providing a detailed study of moving vascular structures. For example, a portion of the proximal wall of an artery may be established as the baseline surface, from which the motion of the distal wall may be differentially measured for the purpose of determining pulsatile changes in vessel diameter. As another example, an inner wall of a ventricle, such as the lateral ventricle in the brain, which is subject to motion caused by CSF pulsation, may be structurally imaged as a moving surface, from which adjacent brain tissue can be referentially imaged without blurring due to the motion of the inner ventricle wall.

Multiple PAS Imaging System with Fixed Antenna Array

Figure 8:
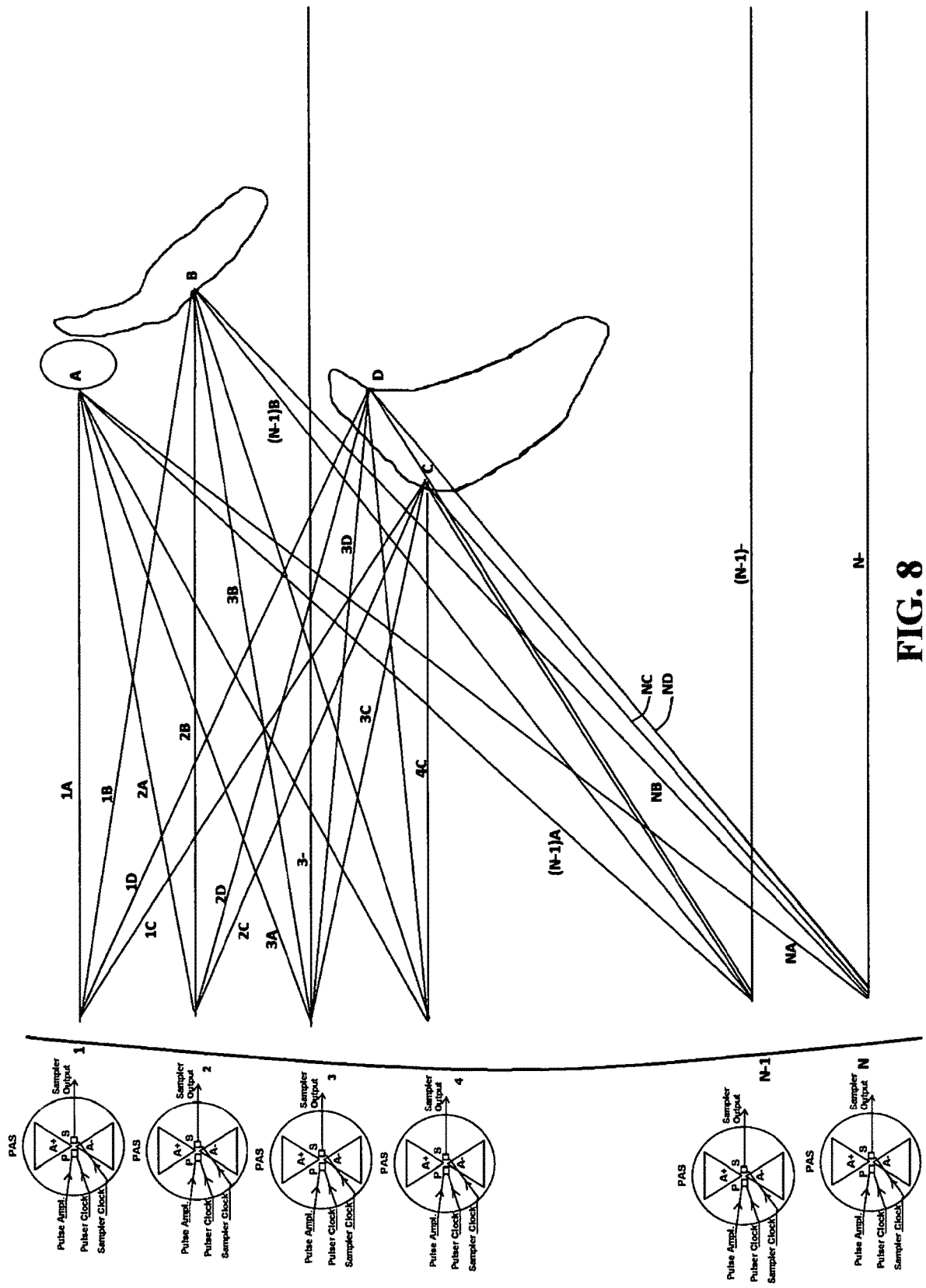
FIG. 8 shows a linear array of pulser/sampler assemblies proximate to a head to illustrate an imaging technique according to an exemplary embodiment of the present invention.

It will be understood that if a sufficient number of PAS assemblies 100 are placed around the region of interest, conventional microwave tomographic inversion, back-projection, and beam forming techniques, in combination with conventional inverse scattering algorithms, will allow complex two-dimensional and three-dimensional images to be constructed from signals received by the multiple PAS assemblies 100. Furthermore, discretized modifications of conventional synthetic aperture radar (SAR) techniques may also be used to construct these images. For example, FIG. 8 illustrates a linear array of N PAS assemblies 100 along a line on the surface of the head. An image can be made by sequentially enabling the pulser 110 on one PAS assembly 100 at a time, while the samplers 120 on all N PAS assemblies 100 collect the reflected signal in response to the pulser 110. Hence, in FIG. 8, initially PAS 1 transmits a series of pulses, while PAS 1 through PAS N collect the received signals. In this example, the central beam of the signal from PAS 1 travels along path 1A toward object A. It reflects off of object A back to PAS 1 along path 1A, as well as reflecting toward path 2A toward PAS 2, and along path 3A toward PAS 3. Similar reflections occur for all receiving PAS assemblies, all the way to path NA for PAS N.

A similar reflection process occurs in response to object B, in which the emitted pulse travels along path 1B toward object B, and reflects back to PAS 1 through PAS N along paths 1B, 2B, 3B, . . . all the way to path NB. Then, PAS assembly 2 takes over the role of pulser 110, transmitting a series of pulses, while PAS assemblies 1 through N collect the received signals. This sequence continues until PAS assembly N acts as the pulser 110, and then repeats indefinitely for the duration of the functional image. The resulting data may be back-projected and processed by conventional inverse scattering algorithms, to produce an image of the internal structures and any variations in reflectivity due to functional activity.

Figure 9:
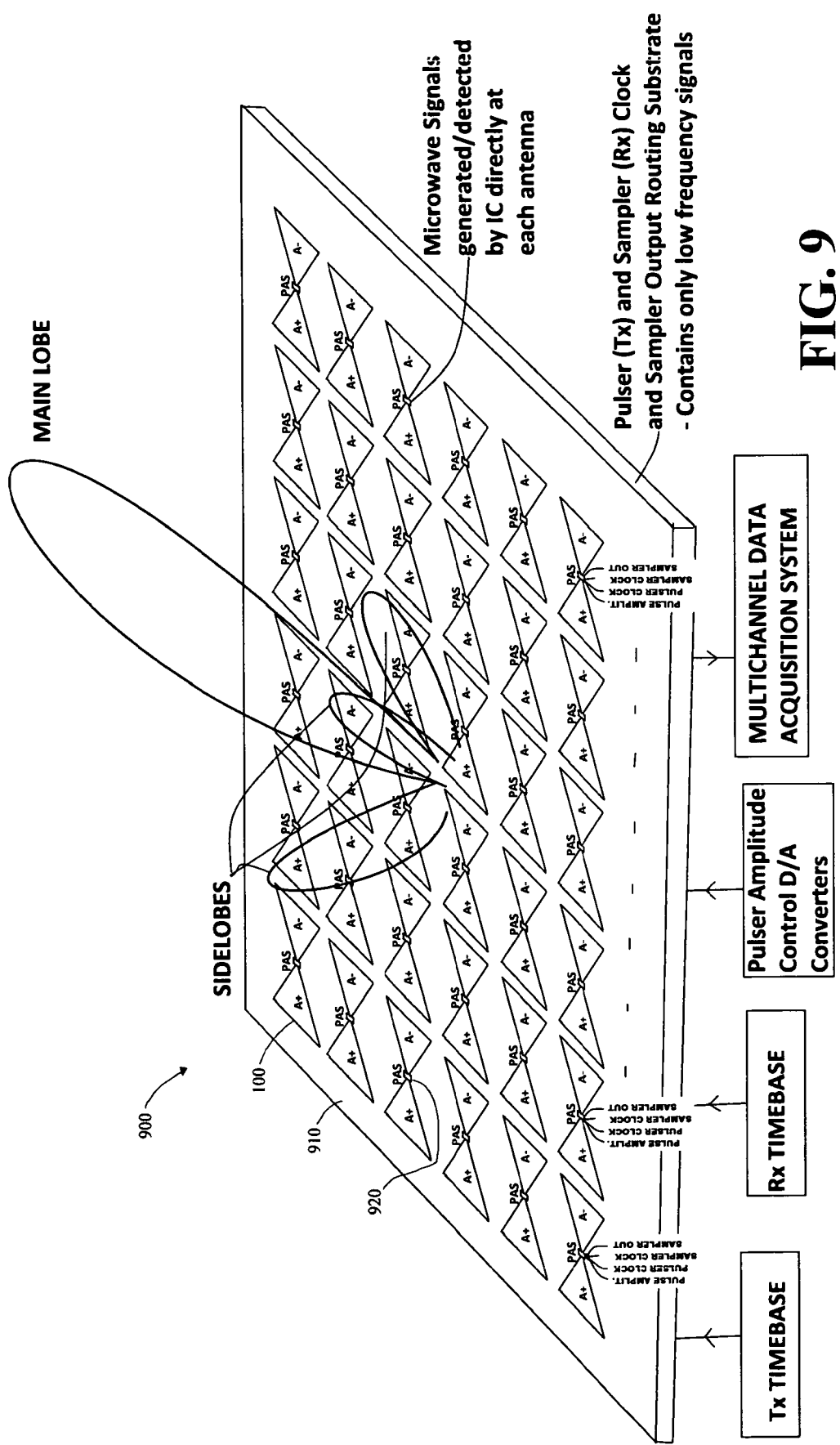
FIG. 9 shows an imager comprising a two-dimensional array of pulser/sampler assemblies according to an exemplary embodiment of the present invention.

The system of FIG. 8 may be extended to utilize a two dimensional planar array of PAS assemblies 100 placed into contact with the body surface of interest, and a sequence of pulses can be emitted by one or more PAS assemblies 100 at a time, while the received echoes are collected by most or all of the PAS assemblies 100. This imager system 900 is illustrated in FIG. 9, and is comprised of an array of PAS assemblies 100 disposed upon or within a substrate 910. In some embodiments, for example, the substrate 910 comprises a helmet shell and the PAS assemblies 100 are attached to the inside surface of the shell, while in other embodiments the PAS assemblies 100 are contained within the substrate 910 so as to be hidden from view. The substrate 910, in some embodiments, is stretchable or formable. As each PAS assembly 100 includes an IC 920 containing both a sampler 120 and a pulser 110, the only wiring required to carry microwave frequencies is located on each PAS assembly 100, and the only other signals transmitted through the system 900 are all low frequency, minimizing cable size and cost. The substrate 910 includes electrically conductive paths sufficient to convey these relatively low-frequency signals to and from the PAS assemblies 100 to provide lower frequency communications to the individual PAS assemblies 100. Such lower frequency signals include those from a pulser clock source 105, typically at a frequency from 1 to 1000 MHz, that are distributed to selected pulsers 110 to form a beam. Each pulser 110 also optionally receives an amplitude-specifying input from a D/A converter 125, which specifies the correct amplitude for that pulser 110 so that the pulser array collectively can form a steered beam. It should be noted that in some embodiments a single D/A converter 125 can serve more than one PAS assembly 100, though one D/A converter 125 for each PAS assembly 100 is described here.

FIG. 9 illustrates an exemplary steered beam consisting of a main lobe and several side lobes. Finally, all samplers 120 are fed with a signal from a common sampler clock 130 that is typically at a slightly lower frequency than the pulser clock 105, as discussed above. The sampler 120 outputs are fed through optional conventional LPFs (not shown) to an array of ADCs 135 whose digital outputs are fed to a computer for reconstruction into an image. The LPFs remove noise components that are of higher frequency than the signal bandwidth needed to produce the image, thus preventing degradation in SNR caused by out-of-band noise. A three-dimensional image can be computed from the digital outputs using conventional back-projection and/or beam-steering algorithms, such as those used in ground penetrating radar (GPR) or phased array radar (PAR) systems.

Figure 10:
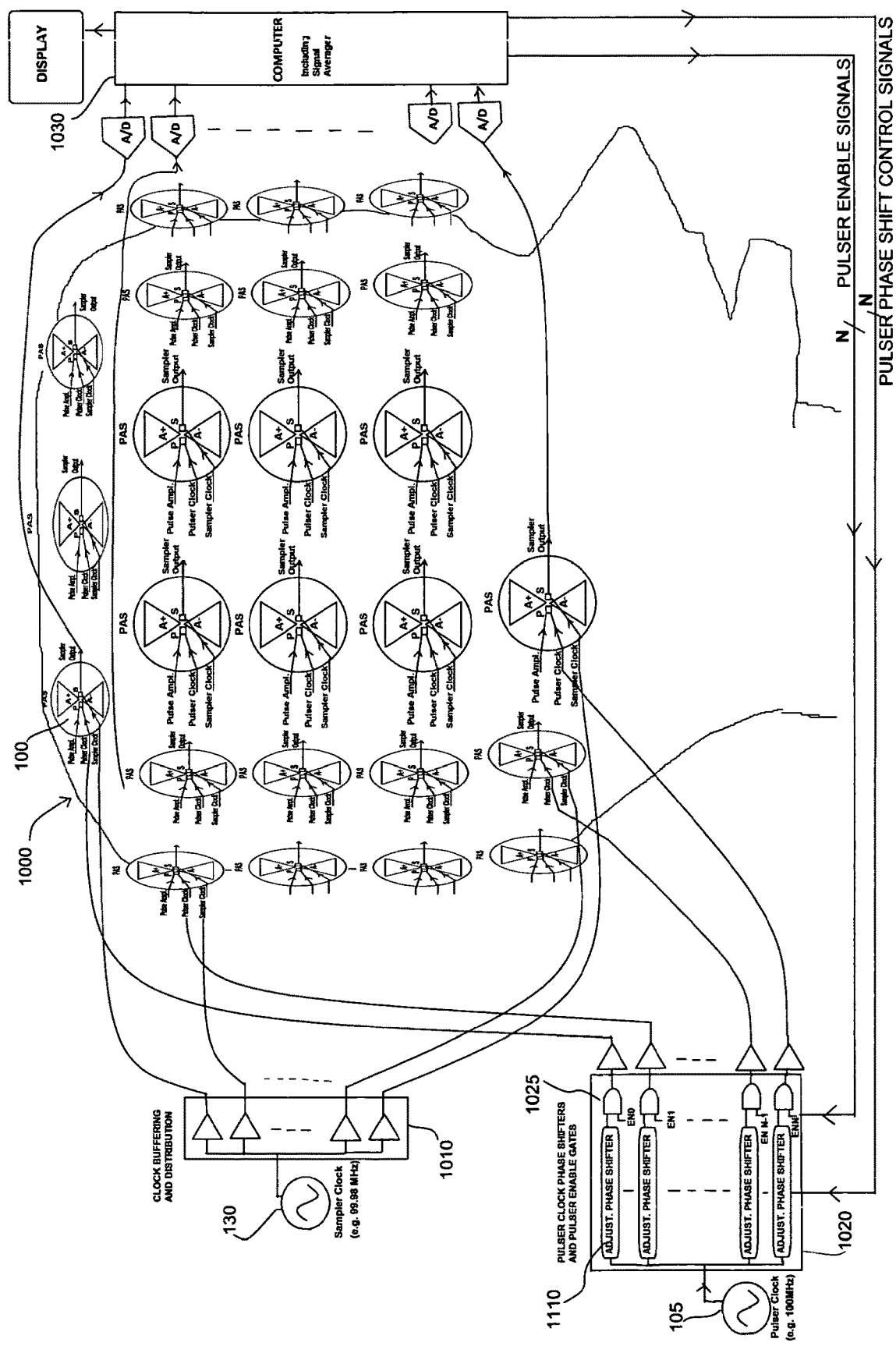
FIG. 10 shows an imager comprising a three-dimensional array of pulser/sampler assemblies arranged within a helmet so as to fit around a head, according to an exemplary embodiment of the present invention.

The architecture of FIG. 9 can be extended into the shape of a cap or helmet, or flexible wrap-around jacket assembly capable of conforming to the heads of a wide range of people, comprised of an array of PAS assemblies 100 surrounding a large area of the head, as shown in FIG. 10, thus enabling imaging a large region of the brain and its associated structures. As with the system 900 of FIG. 9 with its planar substrate 910, the helmet 1000 of FIG. 10 contains a sampler clock 130, and a clock buffering and distribution system 1010, also referred to herein as a sampler controller, whose outputs are fed to the clock inputs of the samplers 120 on the PAS assemblies 100. The buffering system amplifies the relatively weak current of the single sampler clock 130 so that it has sufficient current to concurrently drive all of samplers 120 in the large number of PAS assemblies 100, much like a cable distribution amplifier feeding a large number of television sets in a building. Distribution system 1010 can provide a sampler clock signal to every PAS assembly 100 at the same time, or to a subset of PAS assemblies 100. The signal from a pulser clock 105 is fed to a pulser select controller 1020, whose outputs are fed to the clock inputs of the one or more pulsers 110 that are desired to be activated at a given time.

Additionally, the adjustable phase shifters 1110 in pulser select controller 1020 are configured to individually delay the pulser clock provided to each pulser by an amount needed to achieve a specified phase shift, which in combination with the pulser amplitude-specifying inputs from D/A converter 125 to the selected pulsers 110 then effects the needed superposition of electromagnetic radiation from a given cluster of adjacent pulsers 110 to form a steered beam from those pulsers 110 to target a specific region of the body. The differential balanced architecture of the pulsers 110 allows the pulser amplitude input to also specify pulse output polarity, as described earlier, enabling both positive and negative pulses, of arbitrary amplitude, to be individually specified for each pulser 110 in the array. This pulser configuration, with separate amplitude and phase control (both controlled by a computer) for each pulser 110 in the array, is analogous to the amplitude and phase shift control of the sinusoidally driven array of antennas used to generate a steered beam in a conventional phased array radar. Also, as will be discussed below in respect to FIG. 11, the individual phase shifters in pulser controller 1020 can in some configurations be replaced by a single phase shifter whose values are dynamically altered while signal averaging is taking place on the signals concurrently received from the samplers 120 while the phase shifting sequence is taking place.

The pulser clock controller 1020 further contains AND gates 1025 (such as On Semiconductor MC100EP05), that can be used to completely turn off the pulser clocks 105 for those pulsers 110 that are not being used at a given time. While in theory this would not be needed, as any pulser 110 can be programmed to have zero amplitude by D/A converters 125, in practice there is a small amount of clock feedthrough in any practical pulse generator, which can cause undesired noise in the received signals seen later by the samplers 120. For this reason, unused pulsers 110 can be disabled by turning off their pulser clocks 105, as well as removing the power supplied to them.

A given PAS assembly 100, and neighboring PAS assemblies 100, in some embodiments, generate a string of pulses while all other PAS assemblies 100 receive the reflected and/or transmitted signals. Finally, the outputs of the samplers 120 from the PAS assemblies 100 are optionally lowpass filtered before being provided to an array of ADCs 135 whose outputs are computer processed for reconstruction into an image, optionally using any of a variety of conventional algorithms, such as by computer 1030. By using conventional back-projection, time gating and inverse scattering algorithms, for instance, an image may be reconstructed using the digital output signals from all or most of the PAS assemblies 100. Furthermore, as many of the PAS assemblies 100 may be on the opposite surface of the head, or otherwise in a line of sight to the one or more emitting pulsers 110, some or all of the signals they receive will not be reflections of the pulse (i.e. TDR), but will instead be transmitted versions of the pulse that traverse the head (TDT).

It should be noted that when employing steered beam techniques, while the clock signals fed to the pulsers need to have individually controllable amplitude (including polarity) and phase shift, the samplers do not require similar adjustable clock parameters and instead may all be driven by a single clock signal phase and amplitude. This is because inverse "beam forming" on the received signals from the sampler may all be done using conventional software algorithms, of the type used for conventional phased array radar, which can affect the phase shifting and amplitude weighting without the need for extra hardware.

Figure 11:
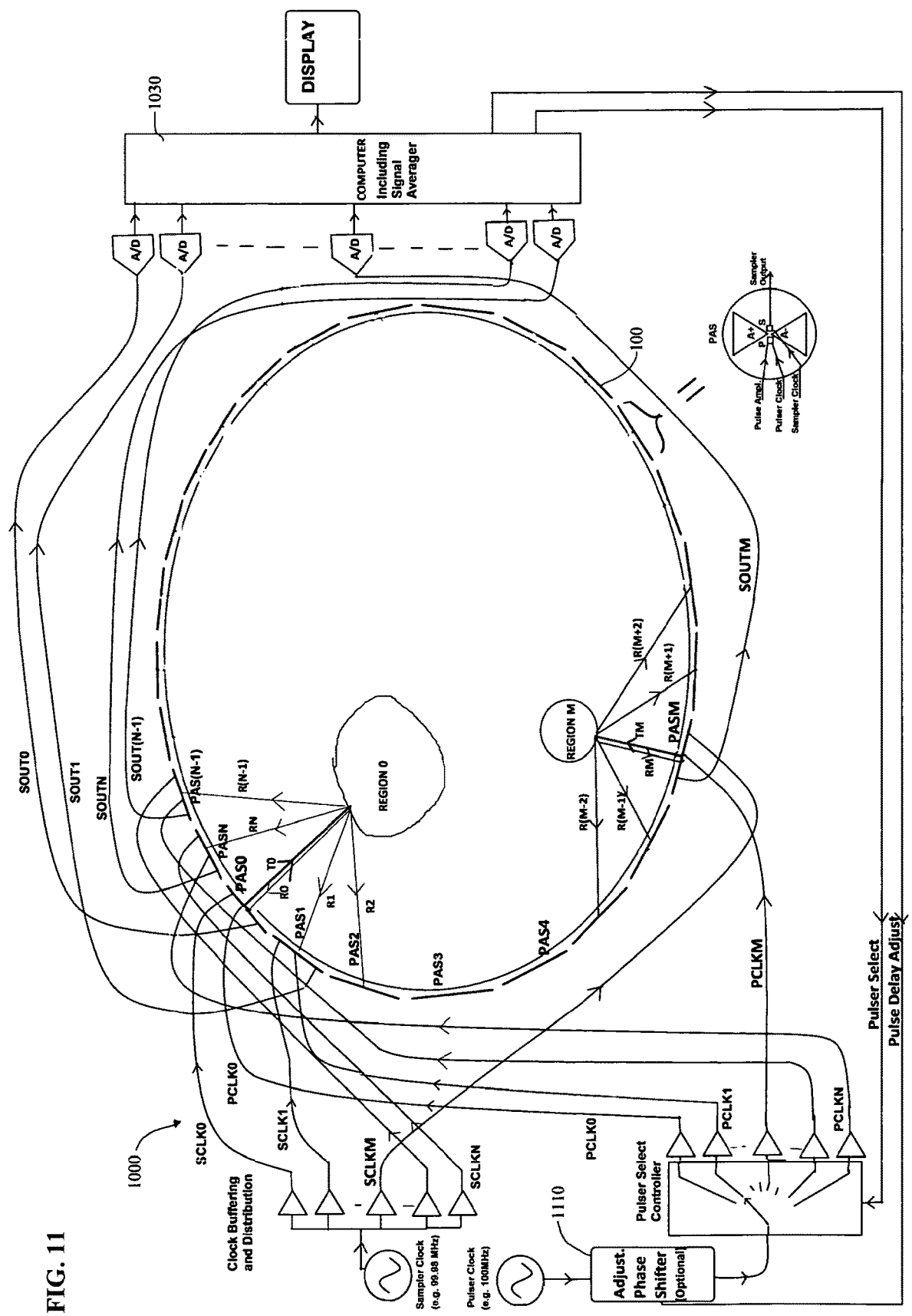
FIG. 11 shows a cross sectional plane of the helmet of FIG. 10 according to an exemplary embodiment of the present invention.

FIG. 11 shows one cross sectional horizontal plane through the helmet 1000 of FIG. 10, which illustrates how an image of a slice of brain can be produced, by separately producing a set of smaller surface images using TDR techniques like those of FIGS. 8 and 9, as shown, and then optionally combining these images. While a single transmitting PAS assembly 100, by virtue of its flat broadband antenna 115 has a wide radiation pattern that lacks directional selectivity, and thus produces a potentially blurred image, it is possible to effect a directed beam in front of each transmit antenna 115 at low cost by using phased array radar techniques. This can be done by activating the pulsers 110 on several adjacent PAS assemblies 100 at once, each with an appropriate amplitude, polarity, and phase to result in the desired beam pattern and direction. This, in turn, can be implemented with multiple phase shifters, one for each pulser 110.

For example, to make a steered beam whose radiation pattern is centered at a given primary pulser 110, that pulser 110 is driven with a high positive amplitude pulse at a given time. Additionally, the surrounding pulsers 110 are driven by pulses of lower amplitude, and slightly different time offsets such that the constructive and destructive interference patterns from the superposition of the radiation patterns from the primary pulser 110 and surrounding pulsers 110 together cause a strong beam emanating at a desired angle. Normally, this conventional approach would require a phase shifter driving the clock input of each pulser 110 as was shown in FIG. 10. However, this is cost inefficient, as the very low cost and size of the pulsers 110 of the current invention are far less than those of the phase shifters. To keep the cost and size of the system at the very low levels enabled by the sampler/pulser ICs, the effect of multiple pulsers 110 and phase shift networks can be emulated using a single adjustable phase shifter 1110, as shown in FIG. 11, whose delay can be changed in a sequence as each pulser 110 is actuated in turn, while the receiving PAS assemblies 100 acquire the received signals, and a computer 1030 average them. Where there is time to average the response of thousands of pulses, it is possible to emulate the superposition of several concurrently operating pulsers 110 with different amplitudes and phases by instead using a single pulser 110 at a time, with a given amplitude and phase, followed by turning that pulser 110 off and activating a second pulser 110 with a different amplitude and phase, and so forth until all of the nearby pulsers 110 have had their turn, all the while the samplers are averaging the resulting signals caused by these pulsers 110. This is done by having the amplitude-setting signals for the active pulsers 110 from DCA converter 125 changed in sequence, as well as the phase shift setting of the single phase shifter 1110 changing in sequence, while the averaging of the returned signals from the body takes place across all of the samplers 120, so as to fully emulate the phase and amplitude configuration of adjacent transmitters in a conventional phased array radar system. Conventional signal processing techniques can be used to compensate for the scattering that occurs as the wavefront from a pulser 110 scatters as it traverses the complex structures in the body before reflecting back to nearby antennae 115.

As the head is large, and significant attenuation occurs as microwave energy traverses its tissues, it is possible to run several concurrent TDR images, without each one interfering with the other. For example, an array of PAS assemblies 100 on the forehead may construct a frontal image, such as that of Region 0 in FIG. 11, while a different array of PAS assemblies 100 at the back of the head can be simultaneously constructing an occipital image, or another array on each side of the head can be constructing concurrent temporal images, such as the one depicted as Region M in FIG. 11.

Figure 12:
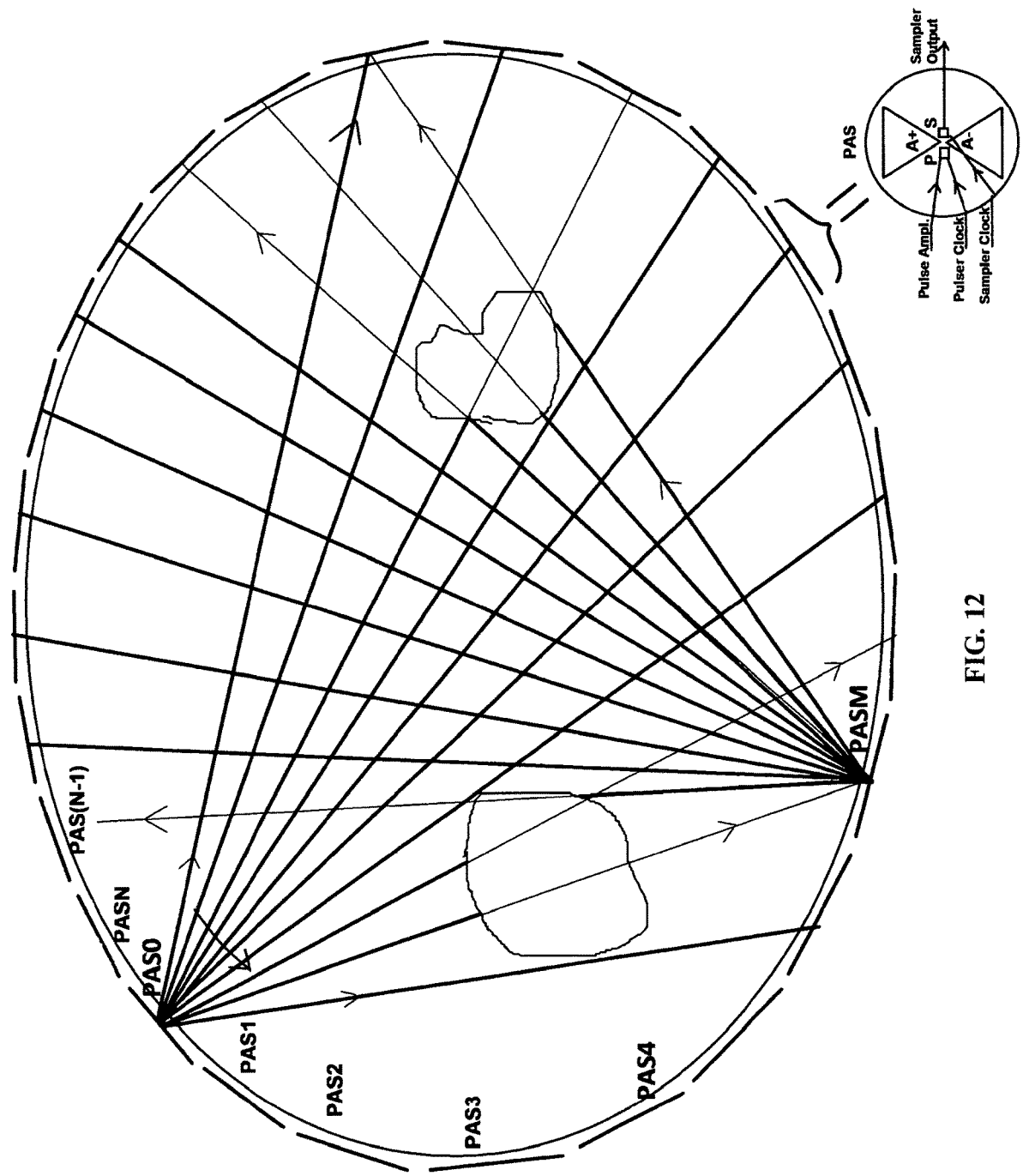
FIG. 12 shows several pulser/sampler assemblies positioned around a head to image various features according to exemplary embodiments of the present invention.

As an alternative, a TDT approach may be used, in which the pulser 110 of a single PAS assembly 100, and optionally those of some neighboring PAS assemblies 100, are activated at a time, and a group of samplers 120 on the opposite side of the head collect the signals that have traveled through the head, as illustrated in FIG. 12. Here, initially PAS0 transmits a series of pulses, while assemblies PAS0 through PASN collect the received signals. The signals from nearby assemblies PAS1, PAS2, PASS, and PASN, PASN-1, PAS2 may be discarded, and only signals on an arc at the opposite surface of the head from the active pulser 100 are used. Time gating algorithms can be used to select only the earliest arriving signals that have presumably traveled the straightest paths, and reject later-arriving signals that have been heavily scattered as they traverse the complex structures in the body before reaching their respective receiving antennae 115.

While there are complications with this simplified approach, such as the fact that signals traveling through tissues with higher $E_r$ (and therefore slower propagation velocities) may arrive later at the receiving PAS Assemblies 100 than signals that have traveled further through tissues with lower $E_r$, it is possible to solve for the dielectric constant at each location when incorporating the data from a sufficiently large number of projection angles.

The TDR operation of the configuration in FIG. 11 can be combined with the TDR operation of the configuration in FIG. 12 to produce images that combine data from both methods. For example, shallow structures may be better imaged using TDR data, while the reflections from deep structures would suffer too much scattering by the time they return to the antennas 115 near the PAS assembly 100 with the active pulser 110. These deep structures can be better imaged, in some instances, by imaging the signals that traverse these structures and are received by the samplers 120 in PAS assemblies 100 across the body. Time gating can be used in this case to reject all signals except those that take the most direct path between transmitter and receiver. As above, time gating is complicated by the fact that different tissue types have different propagation velocities, however, these effects can be taken into account and an image can be produced as described above, by incorporating the data from a sufficient number of projection angles.

Also, conventional inverse scattering methods using a realistic forward model simulation, computation of gradients, and inverse imaging methods may be used to determine the dielectric models for the various tissues. The forward model can be finite difference time domain (FDTD), pseudo-spectral time domain (PSTD), finite element method (FEM), finite element time domain (FETD), diagonal tensor approximation (DTA), discrete dipole approximation (DDA), or implicit methods such as alternating direction implicit FDTD (ADI-FDTD). The forward method may use approximation methods such as the Born approximation. The inverse problem consists of writing a cost function that measures how well the solution of the dielectric parameters match the measured data. The cost function can be optimized by many known methods include Newton's method, Gauss-Newton, quasi-Newton methods, gradient descent, conjugate gradient (and variants that may take advantage of the fast Fourier transform (FFT)), Levenberg-Marquardt, and generalized minimal residual (GMRES). Optimization methods may require a gradient; this can be computed through finite difference or the adjoint method, amongst others known by practitioners in the art. The cost function can include a regularization term that makes the solution less sensitive to noise and numerical difficulties. The regularization function can take on different norms, can be edge preserving, or may be oriented to sparsity.

In particular, an FDTD method may be used with frequency dependent dielectric model to model the UWB effects of the pulses that are generated by the PAS assemblies 100. The dielectric model may be a Debye, Lorenz or Cole-Cole model, for example. The inverse scattering problem will then determine multiple dielectric parameters at each voxel. The adjoint method can find the gradients with respect to the multiple dielectric parameters.

The stochastic gradient method has been used as an optimization method in statistical learning; together with the back-propagation algorithm it is used in training neural networks. The microwave inverse scattering problem can be solved similarly. The adjoint method requires a simulation backward in time for each transmitting antenna 115. Not all backward simulations need be done; single simulations can be done randomly and used to approximate the gradient, or random subsets of the simulations can be used to approximate the gradient. In addition, the cost function can depend on a random subset of PAS assemblies 100 on substrate structure 910. Together, these approximations can substantially reduce the runtime of the inverse problem. Other types of stochastic optimizations can also be used.

Figure 13:
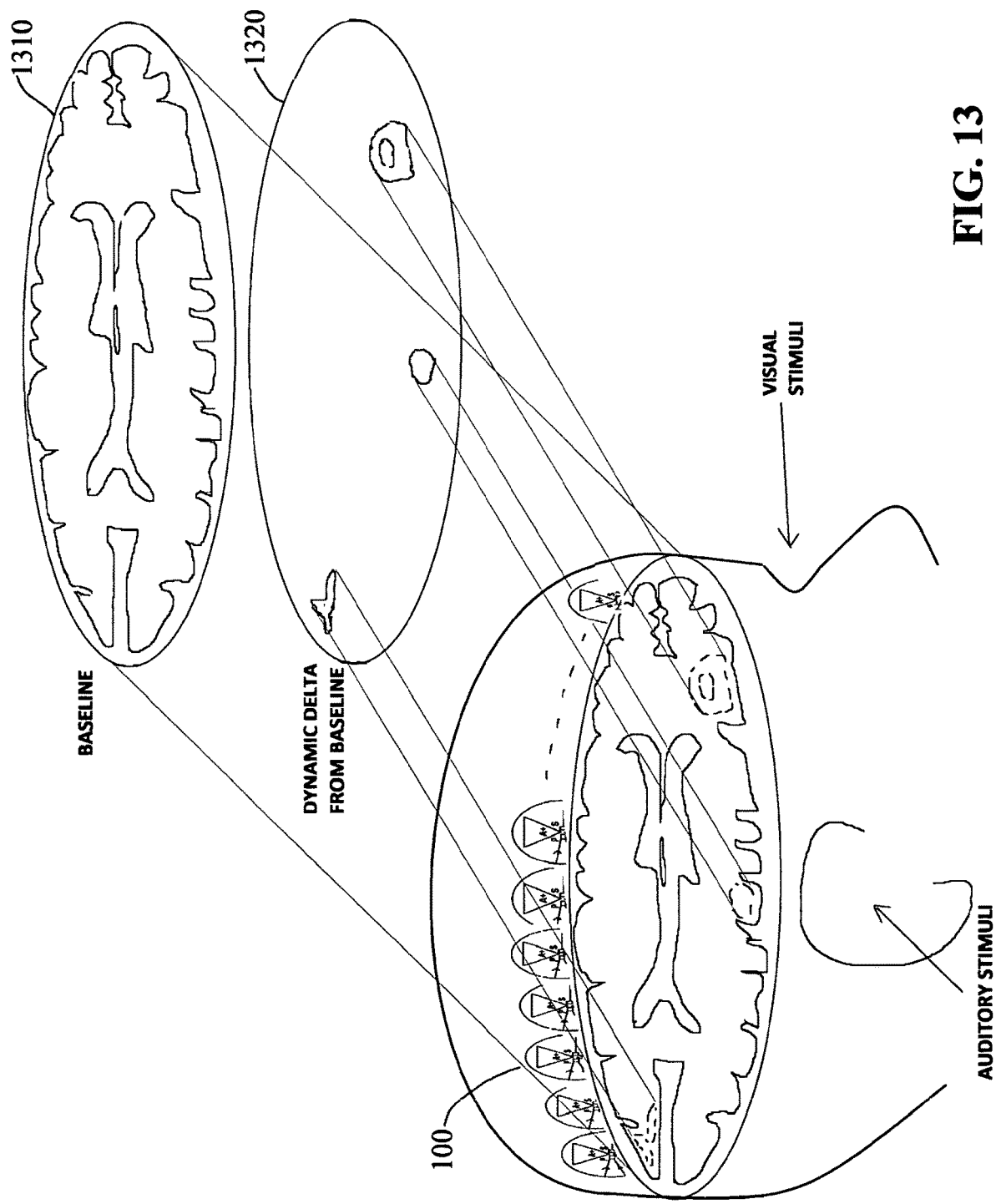
FIG. 13 illustrates both a structural map to serve as a background, and a functional map produced relative to the background according to an exemplary embodiment of the present invention.

Ultimately, the above-described algorithms can be used to produce a set of cross sectional images, such as that shown in FIG. 13, in which a structural image based on dielectric properties of the various tissues can be displayed. It is further possible to show functional activity by using such an image as a baseline image 1310, and then taking a time series of subsequent images and subtracting the baseline image 1310 from each of these subsequent images. In this way, a rapidly sequenced array of PAS assemblies 100 can produce a real-time image of changing mental activity or of pulsation due to changes in arterial and capillary bed pressures. In some embodiments, the baseline image 1310 is established by averaging the reflectivity and/or transmissivity data from an array of PAS assemblies 100, thereby providing an image that primarily contains structural information, by virtue of the fact that small transitory changes due to changing mental activity are largely averaged out.

Next, a new sequence of real-time images is taken in succession, and these new images are subtracted, as they are acquired, from the stored baseline image 1310, yielding a dynamic picture 1320 of metabolic changes or tissue pulsation. In this way, subtle subsequent changes in dielectric properties or tissue pulsation caused by functional activity will show up as differences between these later images and the baseline image 1310. The changes may also be displayed together with the structural baseline image 1310, e.g. overlaid in a different color or pattern. In some embodiments, each such picture 1320 can be acquired in less than 5 milliseconds, and less than 1 millisecond in some embodiments, yielding a real-time spatial image of changing mental activity. When compared to the many minutes required by PET scanners, and the 2-4 seconds required to note changes using fMRI, it will be apparent that those methods cannot display the results of metabolic and neural changes rapidly enough to convey real-time thought processes, while the apparatus and method of the current invention has this capability.

Present neuroprosthetic devices to enable motor activity in persons with spinal injuries have been based on Electroencelography (EEG) and Electrocorticgraphy (ECoG). EEG, while being non-invasive and safe, fails to adequately determine source localization of signals in the brain, and is therefore incapable of providing real-time signals needed for precise control of external motor prosthetics. ECoG relies on the implantation of electrodes on the exposed surface of the brain, and allows greater spatial and temporal precision in localizing spatial sources of signals in the brain. Furthermore, subjects have used this conventional technique to control artificial limbs with little signal processing of the raw electrode signals, and remarkably fast subject training. However, the technique is invasive, with risks of infection and other complications, including electrode failure within two years. More importantly, it is still incapable of indicating the precise location of signals from deeper in the brain. The present invention, being able to utilize the timing of received reflected microwave pulses to localize activity at various depths in the brain, potentially allows for similar control but with far greater spatial resolution and a far richer amount of data to enable the external control of complex motion.

Figure 14:
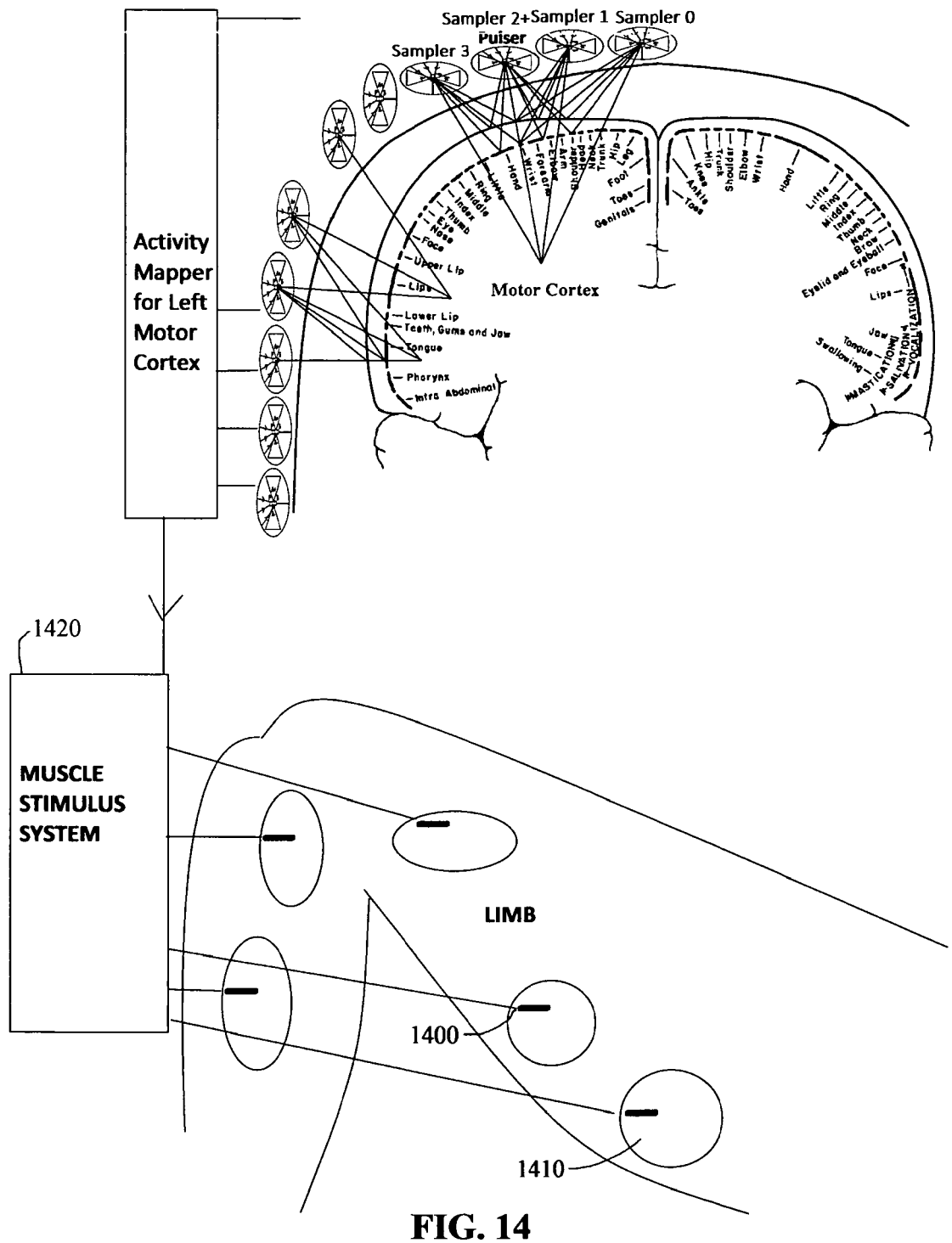
FIG. 14 schematically illustrates how functional imaging of the motor cortex can be used to control muscles in a limb, according to an exemplary embodiment of the present invention.

FIG. 14 illustrates how the present invention can acquire a real-time image of mental activity in a selected region of the brain, in this case, the motor cortex and associated regions of the brain, and this real-time image data can then be computer-processed and used to control electrodes 1400 that stimulate muscles 1410 such as in limbs. In 1951, Wilder Penfield found that activity in specific regions of the motor cortex are mapped to, and precede and cause, motion of specific corresponding muscle groups of the body in a healthy person. Further, as presented in the 2015 DARPA "Wait, What" Conference, a subject, Jan, who had an array of neural electrodes invasively (surgically) implanted in her primary motor cortexes, was able to directly control a robotic arm. Moreover, the simple direct mapping of signals from motor cortex locations to muscles in the arm and hand was sufficient to enable her to control the individual motors in the prostheses. She was able to rapidly self-train herself to effect complex motions of the hand without need for complex circuitry or computer processing between the invasive electrodes in the brain and the motors of the robotic arm. The direct mapping between specific regions in the cortex and specific muscle motions, while not an exact 1 to 1 mapping capable of controlling individual muscle fibers, was sufficient to enable Jan to intentionally move her robotic hand and arm in precise sequences, and to rapidly condition her brain to cause the apparatus to behave according to her wishes.

Embodiments of the present invention, when implemented with a sufficient number of PAS assemblies 100, can provide similar control as enabled by implanted electrodes, but in a safer, non-invasive manner. Referring to FIG. 14, such an array is shown positioned over the primary motor cortex. Pulses from one or more PAS assemblies 100 reflect off gyral surfaces of the cortex and the reflections from each individual surface region is measured by all of the samplers 120 in the PAS assemblies 100, in the manner shown earlier in FIGS. 8, 10, 11 and 13. Conventional A/D converters 135 process signals from the samplers 120 in these PAS assemblies 100 which are then processed with a conventional processor to produce an image of the changing activity on the surface of the motor cortex; signals derived from activity measured at specific points on the image of the motor cortex are used to actuate the muscle stimulus electrodes 1400 in place of the signals from invasive electrodes as in the past. More specifically, control of the electrodes 1400 can be provided by a muscle stimulus system 1420, comprising a processor, that utilizes features in dynamic images 1320 of the surface of the motor cortex to stimulate specific muscles 1410. The muscle stimulus system 1420 analyzes successive dynamic images 1320 for the appearance of peaks signaling functional activity in portions of the motor cortex that normally activate in order to activate that muscle 1410 via the normal neural pathway. Such peaks can be read as the brain seeking to control that muscle 1410, with aspects of the peak or peaks, such as their shape and amplitude, being indicative of aspects of the control, like the degree of desired muscle 1410 contraction.

Similarly, the real-time image data could potentially be used to control a motorized exoskeleton. This configuration can be used by people with severe spinal cord injuries and other conditions such as strokes, so as to bypass the non-functional neural pathways, and convey the information in the motor cortex and process it in a manner that would enable external control of their muscles 1410 or of the actuators of an exoskeleton. Likewise, the invention could, with suitable subsequent signal processing be used to regenerate signals that could be provided to implanted electrodes 1400 in the spinal cord below the location of the damaged neural tissues, thereby re-enabling actual motor functioning.

Similarly, the methods and apparatus of the present invention could be used to indicate specific regions where activity is occurring in the speech centers of the brain, and said information could be used as part of a speech prosthesis. Systems currently exist for re-enabling a degree of speech capability in a patient who has lost the ability to speak due to a blockage or injury between the Broca center in the brain and the nerves that control the vocal chords, mouth and tongue. For example, Frank Guenther at Boston University's Speech Lab uses arrays of implanted electrodes in the speech center of the brain to wirelessly communicate with a computer that then synthesizes speech. However, this invasive approach is limited in its ability, due to the difficulty of implementing a sufficient number of electrodes in the brain, and the need to confine these lifespan-limited electrodes to the surface of the brain.

Figure 15:
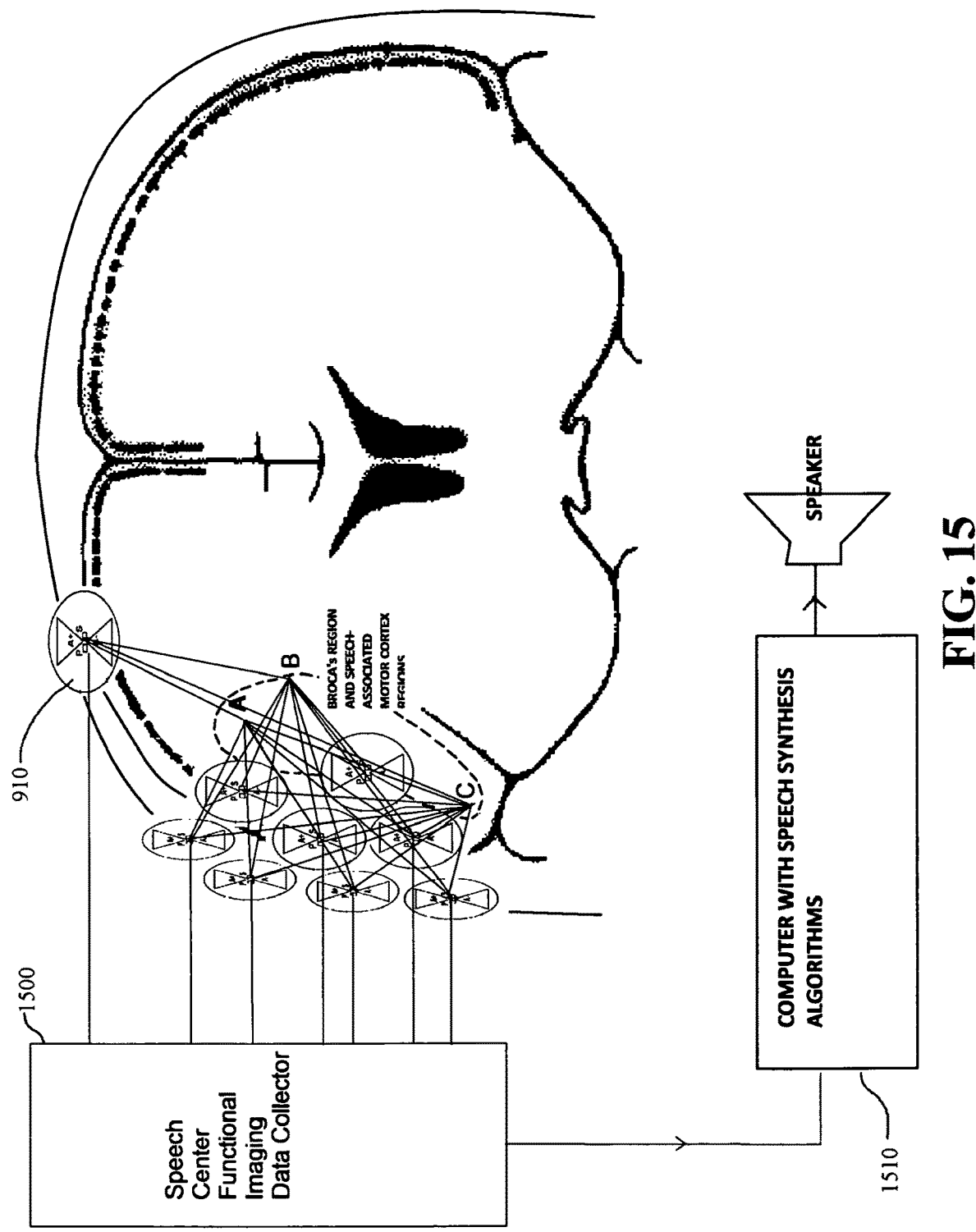
FIG. 15 schematically illustrates how functional imaging of regions of the brain that control speech can be used to synthesize speech, according to an exemplary embodiment of the present invention.

FIG. 15 illustrates how the present invention can be used, as an improved alternative to the use of implanted electrodes, to acquire a real-time image of mental activity in the regions of the brain that control speech, such as the Broca's center and Wernicke's region, and send this real-time reflectivity information to an external computer coupled to an audio DAC to generate synthetic speech based on these time-varying microwave reflectivity images from these brain areas. As above, a speech center functional imaging data collector 1500 can analyze successive dynamic images 1320 for the appearance of peaks signaling functional activity in these speech control portions that activate in combinations and in sequences in order to form spoken words. Additionally, as shown in FIG. 15, the ability to discern activity versus both depth and lateral position relative to the antenna array plane could potentially enable a more sophisticated and complete brain-computer-interface with the for providing improved and more detailed communication between the brain and the vocal prosthesis or speech synthesizer 1510. Locations A, B and C illustrate just three of an almost infinite number of physical locations within the brain that the apparatus of the invention can produce real-time reflectivity data for, by simply transmitting a pulse from one of the PAS assemblies 100, or a cluster of PAS assemblies whose pulsers are driven with suitable amplitudes and phases to effect a steered beam, and receiving the reflection data on some or all of the other PAS assemblies 100. By making each PAS assembly 100 in turn act as the active pulser 110, with the other PAS assemblies 100 providing the samplers 120, a complex image can be reconstructed and used by a computer, having the programming necessary to map specific brain region activity to spoken words, to synthesize speech.

It will be appreciated that the low cost of the PAS assemblies 100 of the current invention could potentially allow upwards of thousands of PAS assemblies 100 to be incorporated into a whole-brain-capable imager, for a cost that is lower than conventional imaging systems such as MRI and CAT scanners. The number of PAS assemblies 100 is limited only by the number of antennas 115, or alternatively RF probes (discussed below), that can cover a surface of interest without interfering with one another.

Figure 16:
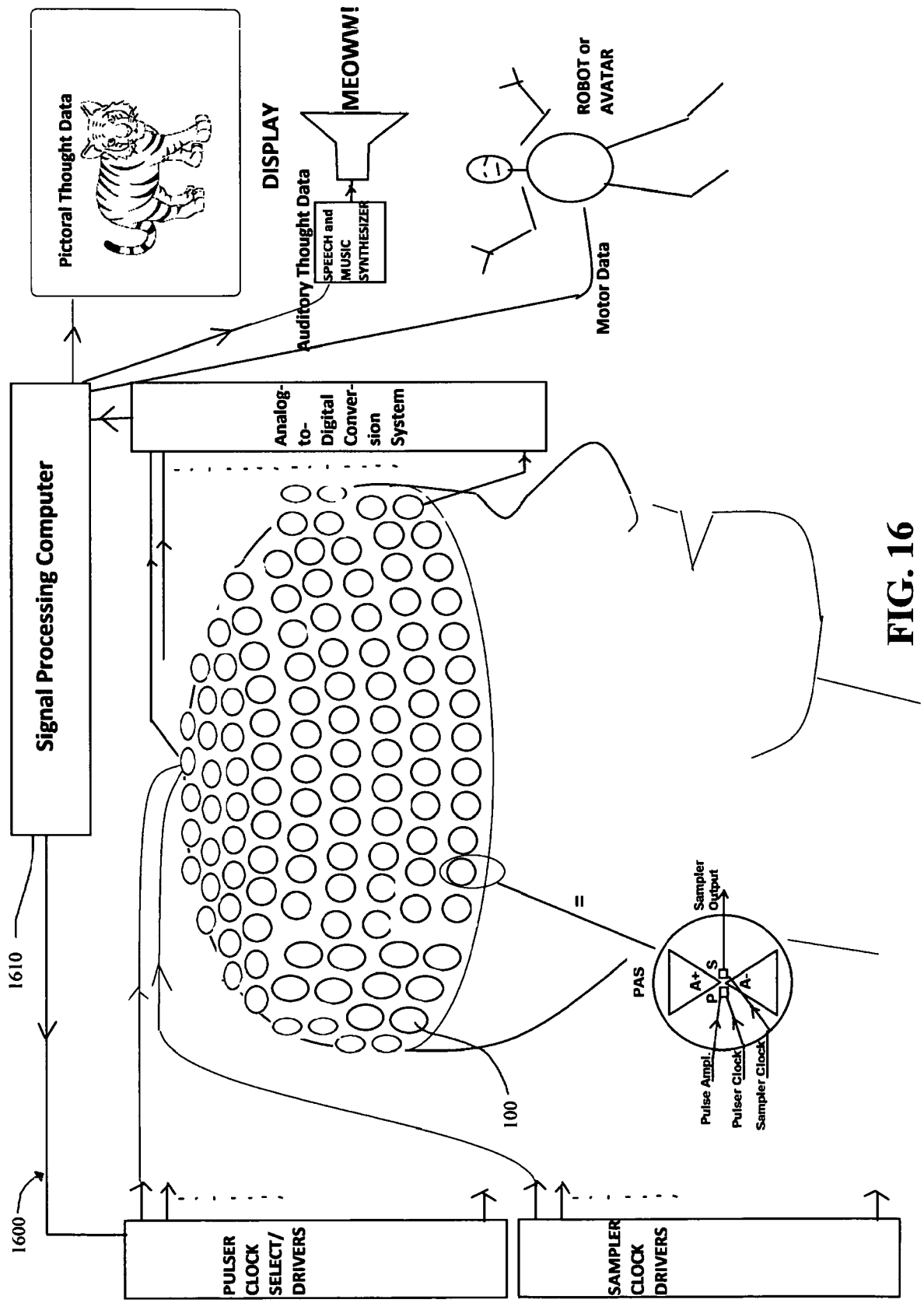
FIG. 16 shows an imager comprising a three-dimensional array of pulser/sampler assemblies and configured to provide an interface for using thoughts to control a speech synthesizer, a visual display, and a robot or avatar, according to an exemplary embodiment of the present invention.

Referring now to FIG. 16, multiple PAS assemblies 100 are combined to provide a multi-element radar cranial imaging apparatus 1600 that can envelope the entire head, and even large regions of the body. As each PAS assembly 100 may be implemented on a single monolithic IC 920 measuring only 2-5 millimeters on each side at the feed points of an antenna 115 typically 1-3 centimeters in diameter, large arrays of identical PAS assemblies 100 can be located in a small cap or helmet, for example, in the cranial imaging apparatus 1600 shown in FIG. 16.

It will be understood that the imaging apparatus 1600, and the other imaging systems described herein, also include components to supply power and control, omitted from the drawings for clarity. For example, imaging systems of the invention include a wiring assembly or substrate that supplies DC power to the PAS assemblies 100 of the array, and a serial control line interface that controls the PAS assemblies 100, either through a star configuration in which a single source is buffered and separately fed to all elements, or through a serial daisy chain method, both of conventional design. The control line interface, which may use conventional serial protocols such as SPI, determines which PAS assemblies 100 on substrate structure 910 emit pulses, and operational settings such as the pulse duration, amplitude, time between pulses, and the frequency difference between the pulser 110 and the sampler 120. The Pulser Select Controller 1020 shown in FIGS. 10 and 11 and Pulser Clock Select/Drivers in FIG. 16 are configured to select which pulser 110 or pulsers 110 of the pulser/sampler assemblies 100 receive transitions to be active at a given time. Additionally, the adjustable phase shifters 1110 discussed earlier are configured to delay the pulser clock provided each pulser by an amount needed to achieve a specified phase shift, which in combination with the pulser amplitude-specifying inputs from D/A converter 125 to the selected pulsers 110 specifies a steered beam from those pulsers 110 to target a specific region of the body.

The imagers of the invention, such as imager 1600, are operated so that each of the N PAS assemblies 100, or alternatively a cluster of PAS assemblies 100 whose pulsers 110 are driven with suitable amplitudes and phases to effect a steered beam, take turns as the active pulser system, while all or most PAS assemblies 100 listen for the returned signals that emanate from the body in response to each pulse. If, for example, 1024 PAS assemblies 100 are used, and each transmits a pulse, then the receiving system will record 1024×1024 distinct strings of one-dimensional signal vectors, each containing the time response at the given receiving antenna 115 resulting from the pulse energy that traverses or reflects from the body. An acquisition time of 100 milliseconds or less can be achieved due to the number of pulses per second, thereby producing a real-time image. For instance, at 100 million pulses per second, using 1024 samplers 120 each concurrently sampling at 99.9 million pulses per second, each sampler 120 will output 100,000 heterodyned waveforms per second, each covering a 10 nanosecond real-time period. As all 1024 samplers are acquired concurrently, the acquisition of each heterodyned waveform takes only 10 microseconds (1 sec/100,000 waveforms). Even if 10 such heterodyned waveforms from each of the 1024 ADCs 135 are averaged together to improve signal to noise ratio, the time to thus fully collect the signal for each pulser 110 turn (the time during which a given pulser 110 is operating) is only 100 microseconds (which is 10 microseconds per waveform, times 10 waveforms averaged). This time is repeated for each of the 1024 pulser 110 turns, resulting in a complete collection time of only about 100 milliseconds.

Applications of Functional Imaging

Scientists are beginning to use conventional functional imaging devices such as fMRI, to produce spatial images that are indicative of a subject's thoughts. For example, neuroscience professor Jack Gallant, of the University of California at Berkeley, has been able to reliably extract, in near-real time, information from a large number of regions of the cortex concurrently, corresponding with the subject's recognition of objects contained in changing visual scenes. However, the ability to extract such though information has been limited by the fact that the fMRI images, which are based on changes in blood flow in volumetric regions in the brain, occur far more slowly than the neural signals that actually underlie thought activity. Moreover, fMRI requires a large, expensive, non-portable system that encases the subject, making it unsuitable for large scale and long-term use by people as they go about their daily activities FIG. 16 illustrates how the invention can be used to provide a real-time image of transmission and reflection data of microwave pulses as they traverse the brain tissues, and the manner in which the resultant spatial image data for selected regions of the brain, including regions of the frontal, parietal, occipital and temporal lobes, can, after computer processing, be displayed on a screen in real time and at a higher speed than the subject could convey this information via speech or manual illustration. In FIG. 16, a large array of PAS assemblies 100, contained in a conformable stretch cap or helmet, rapidly images neural activity in real time, and sends this data to a signal processing computer 1610 to process the data from each region of the brain in a manner appropriate to that region. For example, processed data from the frontal, temporal and occipital lobes of the cerebral cortex could, after a user is suitably trained, be used by him/her to externally portray a visual image of spatially relevant thoughts. Data from the speech centers of the brain could be used to control a speech synthesizer and convey that user's ideas verbally. Additionally, data from the motor cortex regions could control an external robot or avatar analogously to the control of prosthetics as described with respect to FIG. 14.

The invention's potential ability to extract subjective and objective thought activity in a portable implementation of the current invention could form the basis for an imaging system that could facilitate new uses, not possible with prior functional imaging systems. One such example is a social interaction aid, in which users wearing such implementations could communicate conscious and/or unconscious thoughts, feelings and desires from their own brains across Bluetooth, wifi, cellular, and other networks including the Internet, and convey user-selected subsets of their thoughts to others, either directly from the user to another targeted person nearby or at a distance through e-mail or SMS message, or through a social networking program. The system could, for example, be used to facilitate dating, by identifying two users nearby whose brains have, in response to visual cues, both generated functional imaging changes signifying mutual attraction to one another, and then notifying each user of the other user's tentative interest.

Figure 17:
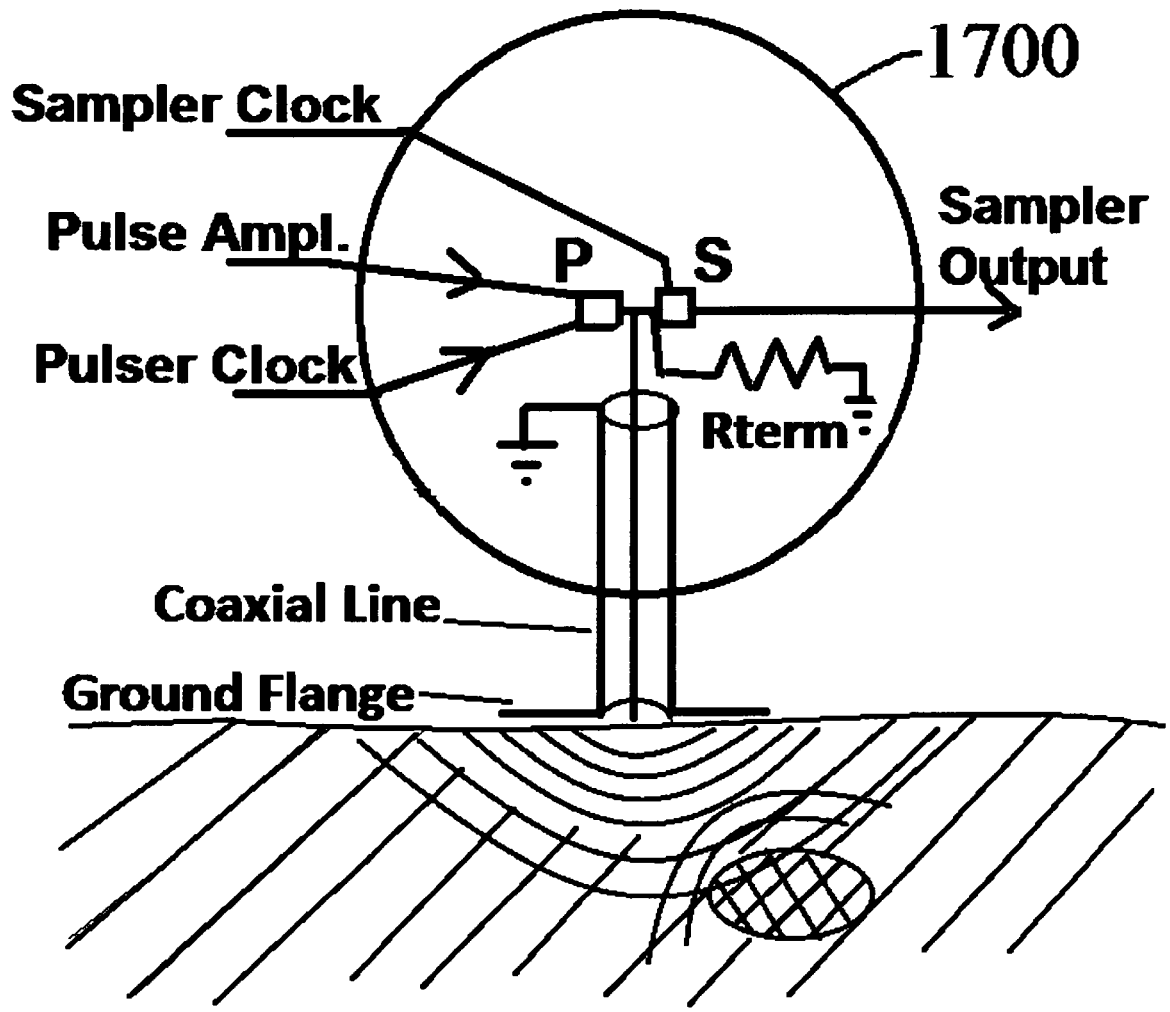
FIG. 17 is a schematic diagram of a pulser/sampler assembly comprising a coaxial line according to an exemplary embodiment of the present invention.
Figure 18:
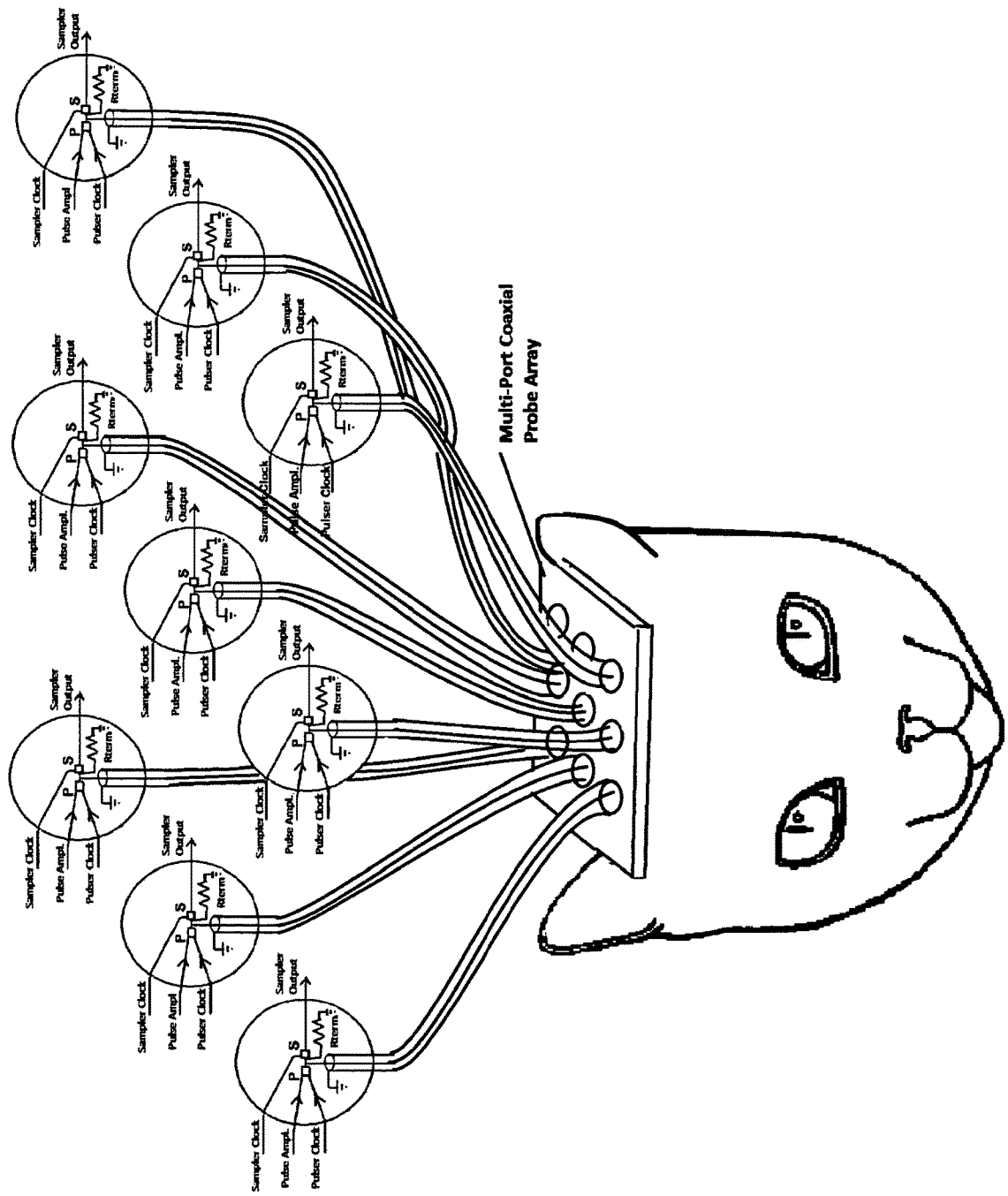
FIG. 18 is a schematic diagram of an array of pulser/sampler assemblies each comprising a coaxial line and arranged around the head of a small animal, according to an exemplary embodiment of the present invention.

One way to greatly increase the antenna packing density when imaging small animals or shallow regions of the brain, such as gyral folds that lie just inside the skull, is to use a coaxial probe 1700 array in place of an array of PAS assemblies 100 with bowtie antennas 115, as shown in FIG. 17. While coaxial probes 1700 have a very limited radiation depth, a coaxial line 1710 with, for example, a 2 mm inner diameter of the outer conductor can provide useful radiation up to 1.5 cm into biological tissue (enabling the viewing of reflections from the relatively shallow gyral folds) and is usable to frequencies over 20 GHz. Allowing for a 1 mm of a flange annulus 1720, this means that one could implement an array of coaxial probes 1700 with a 3 mm center-to-center spacing, potentially allowing an 8×8-element array of such probes over a 1" square scalp region, or up to approximately 10,000 elements over the human scalp, each costing only a few dollars, for extremely high resolution imaging at low cost. In addition to their use for humans, the small size of coaxial probes allows their use in studies on small animals, as illustrated in FIG. 18. It will be apparent to those skilled in the art that other types of conventional microwave or RF probe may be substituted for the coaxial probes shown.

Noise Blending Capability

An array of PAS assemblies 100 can also be used in a noise-blending mode, where multiple PAS assemblies 100 simultaneously transmit different types of pulses; these pulses can simultaneously have different random amplitudes, widths, polarity, and delays. This is a novel use of the unique capabilities of the pulser waveform shaping abilities described above. Previously this has been done in seismic imaging using randomly generated signals or randomly delayed signals. The simultaneous transmission of pulses can dramatically reduce the amount of data necessary for imaging, and reduce the time for gathering an image.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. A method for estimating blood pressure comprising:
using an array of microwave pulser/sampler assemblies positioned around a head or a chest to measure positions of distal and proximal arterial walls of a first artery; and
while measuring the positions of the distal and proximal walls of the first artery
measuring a time difference between
a first time at which a mechanical pulse wave is measured at a first location along the first artery and
a second time at which the same pulse wave is measured at a second location along the first artery, or a second location along a second artery, where the second location is a known path length further from the heart than the first location, wherein
the first time is indicated by measuring a change in a width of the first artery between the distal and proximal arterial walls at the first location and
the second time is indicated
by measuring the same change in a width of the first artery at the second location, or by measuring the same change in a width of the second artery at the second location, and using the known path length difference and the time difference along with a pressure wave transit time algorithm to estimate the blood pressure.

2. The method of claim 1 wherein the array of microwave pulser/sampler assemblies is positioned around the chest, and the first artery comprises a pulmonary artery.

3. A method for estimating blood pressure comprising:

using an array of microwave pulser/sampler assemblies positioned around a head or a chest of a person to measure positions of distal and proximal arterial walls of an artery at a known location; and while measuring the positions of the distal and proximal walls of the artery measuring an EKG of the person, measuring a time difference between a first time of an R wave in the measured EKG, and a second time at which a mechanical pulse wave corresponding to a ventricular contraction whose start is signified by the R wave is measured at the known location along the artery, wherein the second time is indicated by measuring a change in a width of the artery between the distal and proximal arterial walls, and using the known location along the artery and the time difference along with a pressure wave transit time algorithm to estimate the blood pressure.

4. The method of claim 3 wherein the array of microwave pulser/sampler assemblies is positioned around the chest, and wherein the artery comprises a pulmonary artery.

* * * * *